US009878035B2

(12) United States Patent
Du et al.

(10) Patent No.: US 9,878,035 B2
(45) Date of Patent: Jan. 30, 2018

(54) HEPATITIS B VACCINE

(71) Applicant: JIANGSU THERAVAC BIO-PHARMACEUTICAL CO., LTD., Nanjing, Jiangsu (CN)

(72) Inventors: Sean Xiaohan Du, Nanjing (CN); Jun Ge, Nanjing (CN); Xiaoqian Zhuang, Nanjing (CN); Tong Zhou, Nanjing (CN); Jianqiang Li, Nanjing (CN); Cuiling Song, Nanjing (CN); Ying Sun, Nanjing (CN); Meiju Wang, Nanjing (CN); Yue Gu, Nanjing (CN); Honglin Sun, Nanjing (CN); Zhenxing Xu, Nanjing (CN); Hongying Huang, Nanjing (CN); Xiaoxiao Chen, Nanjing (CN)

(73) Assignee: JIANGSU THERAVAC BIO-PHARMACEUTICAL CO., LTD., Nanjing (CN)

( * ) Notice: Subject to any disclaimer, the term of this patent is extended or adjusted under 35 U.S.C. 154(b) by 21 days.

(21) Appl. No.: 14/773,829

(22) PCT Filed: Feb. 26, 2014

(86) PCT No.: PCT/CN2014/072570
§ 371 (c)(1),
(2) Date: Sep. 9, 2015

(87) PCT Pub. No.: WO2014/139359
PCT Pub. Date: Sep. 18, 2014

(65) Prior Publication Data
US 2016/0136264 A1 May 19, 2016

(30) Foreign Application Priority Data
Mar. 13, 2013 (CN) .......................... 2013 1 0080863

(51) Int. Cl.
A61K 39/29 (2006.01)
A61K 39/39 (2006.01)
A61K 39/12 (2006.01)
C12N 7/00 (2006.01)
A61K 39/00 (2006.01)

(52) U.S. Cl.
CPC ............ *A61K 39/292* (2013.01); *A61K 39/12* (2013.01); *A61K 39/39* (2013.01); *C12N 7/00* (2013.01); *A61K 2039/55505* (2013.01); *A61K 2039/55561* (2013.01); *A61K 2039/57* (2013.01); *C12N 2730/10134* (2013.01); *C12N 2730/10171* (2013.01)

(58) Field of Classification Search
None
See application file for complete search history.

(56) References Cited

U.S. PATENT DOCUMENTS

| 6,689,363 B1* | 2/2004 | Sette ...................... C07K 7/06 424/185.1 |
| 7,323,331 B2* | 1/2008 | Maki .................. G01N 33/5762 435/325 |
| 2009/0175904 A1 | 7/2009 | Medina-Selby |
| 2011/0052621 A1 | 3/2011 | Champion et al. |
| 2011/0059132 A1* | 3/2011 | Melber .................. A61K 39/29 424/227.1 |

FOREIGN PATENT DOCUMENTS

| CN | 101492672 | 7/2009 |
| CN | 102462840 | 5/2012 |
| CN | 102612558 | 7/2012 |
| EP | 2484343 | 8/2012 |
| JP | 2008-536515 | 9/2008 |
| JP | 2013-505971 | 2/2013 |
| WO | WO 2006/113528 | 10/2006 |
| WO | WO 2007/031334 | 3/2007 |
| WO | WO 2010/120874 | 10/2010 |

OTHER PUBLICATIONS

Bauer et al., Immunology, 1999, 97:699-705.*
English translation of Xu et al., Zhonghus Yixue Xazhi, 2002, 82(8):553-556, document has 16 pages, Schreiber Translations, Inc., Apr. 2017.*
English machine translation of CN101492672A, 2009, document has 21 pages, ProQuest LLC, 2017.*
Aguilar et al., "Development of a nasal vaccine for chronic hepatitis B infection that uses the ability of hepatitis B core antigen to stimulate a strong Th1 response against hepatitis B surface antigen," *Immunology and Cell Biology*, 82(5):539-546, 2004.
Akbar et al., "Strong and multi-antigen specific immunity by hepatitis B core antigen (HBcAg)-based vaccines in a murine model of chronic hepatitis B: HBcAg is a candidate for a therapeutic vaccine against hepatitis B virus," *Antiviral Research*, 96(1):59-64, 2012.
Bode et al., "CpG DNA as a vaccine adjuvant," *Expert Review of Vaccines*, 10(4):499-511, 2011.
Chu et al., "CpG oligodeoxynucleotides act as adjuvants that switch on T helper 1 (Th1) immunity," *The Journal of Experimental Medicine*, 186(10):1623-1631, 1997.
Extended European Search Report issued in European patent application No. 14765662.3, dated Jul. 27, 2016.
Fujisaki et al., "Outbreak of infections by hepatitis B virus genotype A and transmission of genetic drug resistance in patients coinfected with HIV-1 in Japan," *Journal of Clinical Microbiology*, 49(3):1017-1024, 2011.

(Continued)

*Primary Examiner* — Stacy B Chen
(74) *Attorney, Agent, or Firm* — Parker Highlander PLLC

(57) ABSTRACT

Disclosed is a composition comprising: i) HBsAg, a fragment thereof, a variant thereof, or the mixture of at least two of them, ii) HBcAg1-X, a fragment thereof, a variant of the antigen or the antigen fragment, or the mixture of at least two of them, wherein X is an integer of from 149 to 183, iii) CpG-ODN, 21 bases long, which is a phosphorothioate oligonucleotide and includes two or more copies of 5'-NTCGTT-3' motifs. The use of the composition in the treatment of HBV-infection and HBV-induced diseases, and the therapy methods of HBV-infection and HBV-induced diseases are also disclosed.

9 Claims, 8 Drawing Sheets

(56) References Cited

OTHER PUBLICATIONS

Li et al., "Hepatitis B surface antigen (HBsAg) and core antigen (HBcAg) combine CpG oligodeoxynucletides as a novel therapeutic vaccine for chronic hepatitis B infection," *Vaccine*, 33(35):4247-4254, 2015.

Milich et al., "Role of B cells in antigen presentation of the hepatitis B core," *PNAS*, 94(26):14648-14653, 1997.

Pourkarim et al., "Molecular evolutionary analysis and mutational pattern of full-length genomes of hepatitis B virus isolated from Belgian patients with different clinical manifestations," *Journal of Medical Virology*, 82(3):379-389, 2010.

English translation of Office Communication issued in Japanese Patent Application No. 2015-561921, dated Sep. 6, 2016.

Xu et al., "CpG-ODN is a potential candidate for adjuvant for human vaccines," *Zhonghus Yixue Xazhi*, 82(8):553-556, 2002. (English abstract of Chinese publication).

Chin and Locarnini, "Treatment of chronic hepatitis B: current challenges and future directions," *Rev. Med. Virol.*, 13:255-272, 2003.

English translation of PCT International Search Report and Writen Opinion issued in International Patent Application No. PCT/CN2014/072570, dated Jun. 12, 2014.

Fattovich et al., "Natural history of chronic hepatitis B: Special emphasis on disease progression and prognostic factors," *Journal of Hepatology*, 48:335-352, 2008.

Gong et al., "Insect cell-expressed hemagglutinin with CpG oligodeoxynucleotides plus alum as an adjuvant is a potential pandemic influenza vaccine candidate," *Vaccine*, 30:7498-7505, 2012.

Huang et al., "The Immune Response Induced by Hepatitis B Virus Principal Antigens," *Cellular & Molecular Immunology*, 3(2):97-106, 2006.

Kwon and Lok, "Hepatitis B therapy," *Nat. Rev. Gastroenterol. Hepatol.*, 8:275-284, 2011.

Rath and Devey, "IgG subclass composition of antibodies to HBsAg in circulating immune complexes from patients with hepatitis B virus infections," *Clin. Exp. Immunol.*, 72:164-167, 1998.

Tang and Yu, "Intrauterine infection with hepatitis B virus," *The Lancet*, 335(8684): 302, Feb. 3, 1990.

Wu et al., "Prokaryotic Expression, Purification and Immunogenicity of Fusion Protein of Hepatitis B Virus Core Antigen and PreS1 Antigen," *Chin. J. Biologicals*, 24(3):249-254, 2011. (English abstract of Chinese publication).

Xie et al., "Patients with chronic hepatitis B infection display deficiency of plasmacytoid dendritic cells with reduced expression of TLR9," *Microbes and Infection*, 11:515-523, 2009.

Xu et al., "A Randomized Controlled Phase IIb Trial of Antigen-Antibody Immunogenic Complex Therapeutic Vaccine in Chronic Hepatitis B Patients," *PLoS ONE*, 3(7):E2565, 2008.

Ying et al., "Cellular immunomodulatory effects of large doses of recombinant HBsAG on HBV transgenic mice," *Guangdong Medical Journal*, 7(24):704-706, 2003. (English abstract of Chinese publication).

\* cited by examiner

SEQUENCE LISTING

```
<160> NUMBER OF SEQ ID NOS: 103

<210> SEQ ID NO 1
<211> LENGTH: 226
<212> TYPE: PRT
<213> ORGANISM: Artificial sequence
<220> FEATURE:
<223> OTHER INFORMATION: Synthetic peptide

<400> SEQUENCE: 1

Met Glu Asn Ile Thr Ser Gly Phe Leu Gly Pro Leu Val Leu Gln
1               5                   10                  15

Ala Gly Phe Phe Leu Leu Thr Arg Ile Leu Thr Ile Pro Gln Ser Leu
                20                  25                  30

Asp Ser Trp Trp Thr Ser Leu Asn Phe Leu Gly Gly Ser Pro Val Cys
                35                  40                  45

Leu Gly Gln Asn Ser Gln Ser Pro Thr Ser Asn His Ser Pro Thr Ser
                50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
                100                 105                 110

Ser Thr Thr Thr Ser Thr Gly Pro Cys Lys Thr Cys Thr Thr Pro Ala
                115                 120                 125

Gln Gly Asn Ser Met Phe Pro Ser Cys Cys Cys Thr Lys Pro Thr Asp
                130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
                180                 185                 190

Ser Ala Ile Trp Met Met Trp Tyr Trp Gly Pro Ser Leu Tyr Ser Ile
                195                 200                 205
```

```
Val Ser Pro Phe Ile Pro Leu Leu Pro Ile Phe Phe Cys Leu Trp Val
    210                 215                 220

Tyr Ile
225

<210> SEQ ID NO 2
<211> LENGTH: 183
<212> TYPE: PRT
<213> ORGANISM: Artificial
<220> FEATURE:
<223> OTHER INFORMATION: Synthetic peptide

<400> SEQUENCE: 2

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 3
<211> LENGTH: 21
<212> TYPE: DNA
<213> ORGANISM: Artificial
<220> FEATURE:
<223> OTHER INFORMATION: Synthetic Oligodeoxynucleotide

<400> SEQUENCE: 3
tcgttcgttc gttcgttcgt t                                           21

<210> SEQ ID NO 4
<211> LENGTH: 25
<212> TYPE: DNA
<213> ORGANISM: Artificial
<220> FEATURE:
<223> OTHER INFORMATION: Synthetic Oligodeoxynucleotide

<400> SEQUENCE: 4
tcgttcgttc gttcgttcgt tcgtt                                       25

<210> SEQ ID NO 5
```

```
<211> LENGTH: 21
<212> TYPE: DNA
<213> ORGANISM: Artificial
<220> FEATURE:
<223> OTHER INFORMATION: Synthetic Oligodeoxynucleotide

<400> SEQUENCE: 5
tcgtcgtcgt cgtcgtcgtc g                                            21

<210> SEQ ID NO 6
<211> LENGTH: 20
<212> TYPE: DNA
<213> ORGANISM: Artificial
<220> FEATURE:
<223> OTHER INFORMATION: Synthetic Oligodeoxynucleotide

<400> SEQUENCE: 6
tccatgacgt tcctgacgtt                                              20

<210> SEQ ID NO 7
<211> LENGTH: 15
<212> TYPE: PRT
<213> ORGANISM: Artificial
<220> FEATURE:
<223> OTHER INFORMATION: Synthetic peptide

<400> SEQUENCE: 7

Met Glu Asn Ile Thr Ser Gly Phe Leu Gly Pro Leu Leu Val Leu
1               5                   10                  15

<210> SEQ ID NO 8
<211> LENGTH: 15
<212> TYPE: PRT
<213> ORGANISM: Artificial
<220> FEATURE:
<223> OTHER INFORMATION: Synthetic peptide

<400> SEQUENCE: 8

Thr Ser Gly Phe Leu Gly Pro Leu Leu Val Leu Gln Ala Gly Phe
1               5                   10                  15

<210> SEQ ID NO 9
<211> LENGTH: 15
<212> TYPE: PRT
<213> ORGANISM: Artificial
<220> FEATURE:
<223> OTHER INFORMATION: Synthetic peptide

<400> SEQUENCE: 9

Leu Gly Pro Leu Leu Val Leu Gln Ala Gly Phe Phe Leu Leu Thr
1               5                   10                  15

<210> SEQ ID NO 10
<211> LENGTH: 15
<212> TYPE: PRT
<213> ORGANISM: Artificial
<220> FEATURE:
<223> OTHER INFORMATION: Synthetic peptide

<400> SEQUENCE: 10

Leu Val Leu Gln Ala Gly Phe Phe Leu Leu Thr Arg Ile Leu Thr
1               5                   10                  15

<210> SEQ ID NO 11
<211> LENGTH: 15
<212> TYPE: PRT
<213> ORGANISM: Artificial
```

-continued

```
<220> FEATURE:
<223> OTHER INFORMATION: Synthetic peptide

<400> SEQUENCE: 11

Ala Gly Phe Phe Leu Leu Thr Arg Ile Leu Thr Ile Pro Gln Ser
1               5                   10                  15

<210> SEQ ID NO 12
<211> LENGTH: 15
<212> TYPE: PRT
<213> ORGANISM: Artificial
<220> FEATURE:
<223> OTHER INFORMATION: Synthetic peptide

<400> SEQUENCE: 12

Leu Leu Thr Arg Ile Leu Thr Ile Pro Gln Ser Leu Asp Ser Trp
1               5                   10                  15

<210> SEQ ID NO 13
<211> LENGTH: 15
<212> TYPE: PRT
<213> ORGANISM: Artificial
<220> FEATURE:
<223> OTHER INFORMATION: Synthetic peptide

<400> SEQUENCE: 13

Ile Leu Thr Ile Pro Gln Ser Leu Asp Ser Trp Trp Thr Ser Leu
1               5                   10                  15

<210> SEQ ID NO 14
<211> LENGTH: 15
<212> TYPE: PRT
<213> ORGANISM: Artificial
<220> FEATURE:
<223> OTHER INFORMATION: Synthetic peptide

<400> SEQUENCE: 14

Pro Gln Ser Leu Asp Ser Trp Trp Thr Ser Leu Asn Phe Leu Gly
1               5                   10                  15

<210> SEQ ID NO 15
<211> LENGTH: 15
<212> TYPE: PRT
<213> ORGANISM: Artificial
<220> FEATURE:
<223> OTHER INFORMATION: Synthetic peptide

<400> SEQUENCE: 15

Asp Ser Trp Trp Thr Ser Leu Asn Phe Leu Gly Gly Ser Pro Val
1               5                   10                  15

<210> SEQ ID NO 16
<211> LENGTH: 15
<212> TYPE: PRT
<213> ORGANISM: Artificial
<220> FEATURE:
<223> OTHER INFORMATION: Synthetic peptide

<400> SEQUENCE: 16

Thr Ser Leu Asn Phe Leu Gly Gly Ser Pro Val Cys Leu Gly Gln
1               5                   10                  15

<210> SEQ ID NO 17
<211> LENGTH: 15
<212> TYPE: PRT
<213> ORGANISM: Artificial
<220> FEATURE:
```

<223> OTHER INFORMATION: Synthetic peptide

<400> SEQUENCE: 17

Phe Leu Gly Gly Ser Pro Val Cys Leu Gly Gln Asn Ser Gln Ser
1               5                   10                  15

<210> SEQ ID NO 18
<211> LENGTH: 15
<212> TYPE: PRT
<213> ORGANISM: Artificial
<220> FEATURE:
<223> OTHER INFORMATION: Synthetic peptide

<400> SEQUENCE: 18

Ser Pro Val Cys Leu Gly Gln Asn Ser Gln Ser Pro Thr Ser Asn
1               5                   10                  15

<210> SEQ ID NO 19
<211> LENGTH: 15
<212> TYPE: PRT
<213> ORGANISM: Artificial
<220> FEATURE:
<223> OTHER INFORMATION: Synthetic peptide

<400> SEQUENCE: 19

Leu Gly Gln Asn Ser Gln Ser Pro Thr Ser Asn His Ser Pro Thr
1               5                   10                  15

<210> SEQ ID NO 20
<211> LENGTH: 15
<212> TYPE: PRT
<213> ORGANISM: Artificial
<220> FEATURE:
<223> OTHER INFORMATION: Synthetic peptide

<400> SEQUENCE: 20

Ser Gln Ser Pro Thr Ser Asn His Ser Pro Thr Ser Cys Pro Pro
1               5                   10                  15

<210> SEQ ID NO 21
<211> LENGTH: 15
<212> TYPE: PRT
<213> ORGANISM: Artificial
<220> FEATURE:
<223> OTHER INFORMATION: Synthetic peptide

<400> SEQUENCE: 21

Thr Ser Asn His Ser Pro Thr Ser Cys Pro Pro Ile Cys Pro Gly
1               5                   10                  15

<210> SEQ ID NO 22
<211> LENGTH: 15
<212> TYPE: PRT
<213> ORGANISM: Artificial
<220> FEATURE:
<223> OTHER INFORMATION: Synthetic peptide

<400> SEQUENCE: 22

Ser Pro Thr Ser Cys Pro Pro Ile Cys Pro Gly Tyr Arg Trp Met
1               5                   10                  15

<210> SEQ ID NO 23
<211> LENGTH: 15
<212> TYPE: PRT
<213> ORGANISM: Artificial
<220> FEATURE:
<223> OTHER INFORMATION: Synthetic peptide

<400> SEQUENCE: 23

Cys Pro Pro Ile Cys Pro Gly Tyr Arg Trp Met Cys Leu Arg Arg
1               5                   10                  15

<210> SEQ ID NO 24
<211> LENGTH: 15
<212> TYPE: PRT
<213> ORGANISM: Artificial
<220> FEATURE:
<223> OTHER INFORMATION: Synthetic peptide

<400> SEQUENCE: 24

Cys Pro Gly Tyr Arg Trp Met Cys Leu Arg Arg Phe Ile Ile Phe
1               5                   10                  15

<210> SEQ ID NO 25
<211> LENGTH: 15
<212> TYPE: PRT
<213> ORGANISM: Artificial
<220> FEATURE:
<223> OTHER INFORMATION: Synthetic peptide

<400> SEQUENCE: 25

Arg Trp Met Cys Leu Arg Arg Phe Ile Ile Phe Leu Phe Ile Leu
1               5                   10                  15

<210> SEQ ID NO 26
<211> LENGTH: 15
<212> TYPE: PRT
<213> ORGANISM: Artificial
<220> FEATURE:
<223> OTHER INFORMATION: Synthetic peptide

<400> SEQUENCE: 26

Leu Arg Arg Phe Ile Ile Phe Leu Phe Ile Leu Leu Leu Cys Leu
1               5                   10                  15

<210> SEQ ID NO 27
<211> LENGTH: 15
<212> TYPE: PRT
<213> ORGANISM: Artificial
<220> FEATURE:
<223> OTHER INFORMATION: Synthetic peptide

<400> SEQUENCE: 27

Ile Ile Phe Leu Phe Ile Leu Leu Leu Cys Leu Ile Phe Leu Leu
1               5                   10                  15

<210> SEQ ID NO 28
<211> LENGTH: 15
<212> TYPE: PRT
<213> ORGANISM: Artificial
<220> FEATURE:
<223> OTHER INFORMATION: Synthetic peptide

<400> SEQUENCE: 28

Phe Ile Leu Leu Leu Cys Leu Ile Phe Leu Leu Val Leu Leu Asp
1               5                   10                  15

<210> SEQ ID NO 29
<211> LENGTH: 15
<212> TYPE: PRT
<213> ORGANISM: Artificial
<220> FEATURE:
<223> OTHER INFORMATION: Synthetic peptide

<400> SEQUENCE: 29

Leu Cys Leu Ile Phe Leu Leu Val Leu Leu Asp Tyr Gln Gly Met
1               5                   10                  15

<210> SEQ ID NO 30
<211> LENGTH: 15
<212> TYPE: PRT
<213> ORGANISM: Artificial
<220> FEATURE:
<223> OTHER INFORMATION: Synthetic peptide

<400> SEQUENCE: 30

Phe Leu Leu Val Leu Leu Asp Tyr Gln Gly Met Leu Pro Val Cys
1               5                   10                  15

<210> SEQ ID NO 31
<211> LENGTH: 15
<212> TYPE: PRT
<213> ORGANISM: Artificial
<220> FEATURE:
<223> OTHER INFORMATION: Synthetic peptide

<400> SEQUENCE: 31

Leu Leu Asn Tyr Gln Gly Met Leu Pro Val Cys Pro Leu Ile Pro
1               5                   10                  15

<210> SEQ ID NO 32
<211> LENGTH: 15
<212> TYPE: PRT
<213> ORGANISM: Artificial
<220> FEATURE:
<223> OTHER INFORMATION: Synthetic peptide

<400> SEQUENCE: 32

Gln Gly Met Leu Pro Val Cys Pro Leu Ile Pro Gly Ser Thr Thr
1               5                   10                  15

<210> SEQ ID NO 33
<211> LENGTH: 15
<212> TYPE: PRT
<213> ORGANISM: Artificial
<220> FEATURE:
<223> OTHER INFORMATION: Synthetic peptide

<400> SEQUENCE: 33

Pro Val Cys Pro Leu Ile Pro Gly Ser Thr Thr Thr Ser Thr Gly
1               5                   10                  15

<210> SEQ ID NO 34
<211> LENGTH: 15
<212> TYPE: PRT
<213> ORGANISM: Artificial
<220> FEATURE:
<223> OTHER INFORMATION: Synthetic peptide

<400> SEQUENCE: 34

Leu Ile Pro Gly Ser Thr Thr Thr Ser Thr Gly Pro Cys Lys Thr
1               5                   10                  15

<210> SEQ ID NO 35
<211> LENGTH: 15
<212> TYPE: PRT
<213> ORGANISM: Artificial
<220> FEATURE:
<223> OTHER INFORMATION: Synthetic peptide

<400> SEQUENCE: 35

```
Ser Thr Thr Thr Ser Thr Gly Pro Cys Lys Thr Cys Thr Thr Pro
1               5                   10                  15

<210> SEQ ID NO 36
<211> LENGTH: 15
<212> TYPE: PRT
<213> ORGANISM: Artificial
<220> FEATURE:
<223> OTHER INFORMATION: Synthetic peptide

<400> SEQUENCE: 36

Ser Thr Gly Pro Cys Lys Thr Cys Thr Thr Pro Ala Gln Gly Asn
1               5                   10                  15

<210> SEQ ID NO 37
<211> LENGTH: 15
<212> TYPE: PRT
<213> ORGANISM: Artificial
<220> FEATURE:
<223> OTHER INFORMATION: Synthetic peptide

<400> SEQUENCE: 37

Cys Lys Thr Cys Thr Thr Pro Ala Gln Gly Asn Ser Met Phe Pro
1               5                   10                  15

<210> SEQ ID NO 38
<211> LENGTH: 15
<212> TYPE: PRT
<213> ORGANISM: Artificial
<220> FEATURE:
<223> OTHER INFORMATION: Synthetic peptide

<400> SEQUENCE: 38

Thr Thr Pro Ala Gln Gly Asn Ser Met Phe Pro Ser Cys Cys Cys
1               5                   10                  15

<210> SEQ ID NO 39
<211> LENGTH: 15
<212> TYPE: PRT
<213> ORGANISM: Artificial
<220> FEATURE:
<223> OTHER INFORMATION: Synthetic peptide

<400> SEQUENCE: 39

Gln Gly Asn Ser Met Phe Pro Ser Cys Cys Cys Thr Lys Pro Thr
1               5                   10                  15

<210> SEQ ID NO 40
<211> LENGTH: 15
<212> TYPE: PRT
<213> ORGANISM: Artificial
<220> FEATURE:
<223> OTHER INFORMATION: Synthetic peptide

<400> SEQUENCE: 40

Met Phe Pro Ser Cys Cys Cys Thr Lys Pro Thr Asp Gly Asn Cys
1               5                   10                  15

<210> SEQ ID NO 41
<211> LENGTH: 15
<212> TYPE: PRT
<213> ORGANISM: Artificial
<220> FEATURE:
<223> OTHER INFORMATION: Synthetic peptide

<400> SEQUENCE: 41
```

```
Cys Cys Cys Thr Lys Pro Thr Asp Gly Asn Cys Thr Cys Ile Pro
1               5                   10                  15
```

<210> SEQ ID NO 42
<211> LENGTH: 15
<212> TYPE: PRT
<213> ORGANISM: Artificial
<220> FEATURE:
<223> OTHER INFORMATION: Synthetic peptide

<400> SEQUENCE: 42

```
Lys Pro Thr Asp Gly Asn Cys Thr Cys Ile Pro Ile Pro Ser Ser
1               5                   10                  15
```

<210> SEQ ID NO 43
<211> LENGTH: 15
<212> TYPE: PRT
<213> ORGANISM: Artificial
<220> FEATURE:
<223> OTHER INFORMATION: Synthetic peptide

<400> SEQUENCE: 43

```
Gly Asn Cys Thr Cys Ile Pro Ile Pro Ser Ser Trp Ala Phe Ala
1               5                   10                  15
```

<210> SEQ ID NO 44
<211> LENGTH: 15
<212> TYPE: PRT
<213> ORGANISM: Artificial
<220> FEATURE:
<223> OTHER INFORMATION: Synthetic peptide

<400> SEQUENCE: 44

```
Cys Ile Pro Ile Pro Ser Ser Trp Ala Phe Ala Lys Tyr Leu Trp
1               5                   10                  15
```

<210> SEQ ID NO 45
<211> LENGTH: 15
<212> TYPE: PRT
<213> ORGANISM: Artificial
<220> FEATURE:
<223> OTHER INFORMATION: Synthetic peptide

<400> SEQUENCE: 45

```
Pro Ser Ser Trp Ala Phe Ala Lys Tyr Leu Trp Glu Trp Ala Ser
1               5                   10                  15
```

<210> SEQ ID NO 46
<211> LENGTH: 15
<212> TYPE: PRT
<213> ORGANISM: Artificial
<220> FEATURE:
<223> OTHER INFORMATION: Synthetic peptide

<400> SEQUENCE: 46

```
Ala Phe Ala Lys Tyr Leu Trp Glu Trp Ala Ser Val Arg Phe Ser
1               5                   10                  15
```

<210> SEQ ID NO 47
<211> LENGTH: 15
<212> TYPE: PRT
<213> ORGANISM: Artificial
<220> FEATURE:
<223> OTHER INFORMATION: Synthetic peptide

<400> SEQUENCE: 47

```
Tyr Leu Trp Glu Trp Ala Ser Val Arg Phe Ser Trp Leu Ser Leu
```

-continued

```
<210> SEQ ID NO 48
<211> LENGTH: 15
<212> TYPE: PRT
<213> ORGANISM: Artificial
<220> FEATURE:
<223> OTHER INFORMATION: Synthetic peptide

<400> SEQUENCE: 48

Trp Ala Ser Val Arg Phe Ser Trp Leu Ser Leu Leu Val Pro Phe
1               5                   10                  15

<210> SEQ ID NO 49
<211> LENGTH: 15
<212> TYPE: PRT
<213> ORGANISM: Artificial
<220> FEATURE:
<223> OTHER INFORMATION: Synthetic peptide

<400> SEQUENCE: 49

Arg Phe Ser Trp Leu Ser Leu Leu Val Pro Phe Val Gln Trp Phe
1               5                   10                  15

<210> SEQ ID NO 50
<211> LENGTH: 15
<212> TYPE: PRT
<213> ORGANISM: Artificial
<220> FEATURE:
<223> OTHER INFORMATION: Synthetic peptide

<400> SEQUENCE: 50

Leu Ser Leu Leu Val Pro Phe Val Gln Trp Phe Val Gly Leu Ser
1               5                   10                  15

<210> SEQ ID NO 51
<211> LENGTH: 15
<212> TYPE: PRT
<213> ORGANISM: Artificial
<220> FEATURE:
<223> OTHER INFORMATION: Synthetic peptide

<400> SEQUENCE: 51

Val Pro Phe Val Gln Trp Phe Val Gly Leu Ser Pro Thr Val Trp
1               5                   10                  15

<210> SEQ ID NO 52
<211> LENGTH: 15
<212> TYPE: PRT
<213> ORGANISM: Artificial
<220> FEATURE:
<223> OTHER INFORMATION: Synthetic peptide

<400> SEQUENCE: 52

Gln Trp Phe Val Gly Leu Ser Pro Thr Val Trp Leu Ser Ala Ile
1               5                   10                  15

<210> SEQ ID NO 53
<211> LENGTH: 15
<212> TYPE: PRT
<213> ORGANISM: Artificial
<220> FEATURE:
<223> OTHER INFORMATION: Synthetic peptide

<400> SEQUENCE: 53

Gly Leu Ser Pro Thr Val Trp Leu Ser Ala Ile Trp Met Met Trp
1               5                   10                  15
```

```
<210> SEQ ID NO 54
<211> LENGTH: 15
<212> TYPE: PRT
<213> ORGANISM: Artificial
<220> FEATURE:
<223> OTHER INFORMATION: Synthetic peptide

<400> SEQUENCE: 54

Thr Val Trp Leu Ser Ala Ile Trp Met Met Trp Tyr Trp Gly Pro
1               5                   10                  15

<210> SEQ ID NO 55
<211> LENGTH: 15
<212> TYPE: PRT
<213> ORGANISM: Artificial
<220> FEATURE:
<223> OTHER INFORMATION: Synthetic peptide

<400> SEQUENCE: 55

Ser Ala Ile Trp Met Met Trp Tyr Trp Gly Pro Ser Leu Tyr Ser
1               5                   10                  15

<210> SEQ ID NO 56
<211> LENGTH: 15
<212> TYPE: PRT
<213> ORGANISM: Artificial
<220> FEATURE:
<223> OTHER INFORMATION: Synthetic peptide

<400> SEQUENCE: 56

Met Met Trp Tyr Trp Gly Pro Ser Leu Tyr Ser Ile Val Ser Pro
1               5                   10                  15

<210> SEQ ID NO 57
<211> LENGTH: 15
<212> TYPE: PRT
<213> ORGANISM: Artificial
<220> FEATURE:
<223> OTHER INFORMATION: Synthetic peptide

<400> SEQUENCE: 57

Trp Gly Pro Ser Leu Tyr Ser Ile Val Ser Pro Phe Ile Pro Leu
1               5                   10                  15

<210> SEQ ID NO 58
<211> LENGTH: 15
<212> TYPE: PRT
<213> ORGANISM: Artificial
<220> FEATURE:
<223> OTHER INFORMATION: Synthetic peptide

<400> SEQUENCE: 58

Leu Tyr Ser Ile Val Ser Pro Phe Ile Pro Leu Leu Pro Ile Phe
1               5                   10                  15

<210> SEQ ID NO 59
<211> LENGTH: 15
<212> TYPE: PRT
<213> ORGANISM: Artificial
<220> FEATURE:
<223> OTHER INFORMATION: Synthetic peptide

<400> SEQUENCE: 59

Val Ser Pro Phe Ile Pro Leu Leu Pro Ile Phe Phe Cys Leu Trp
1               5                   10                  15
```

```
<210> SEQ ID NO 60
<211> LENGTH: 14
<212> TYPE: PRT
<213> ORGANISM: Artificial
<220> FEATURE:
<223> OTHER INFORMATION: Synthetic peptide

<400> SEQUENCE: 60

Ile Pro Leu Leu Pro Ile Phe Phe Cys Leu Trp Val Tyr Ile
1               5                   10

<210> SEQ ID NO 61
<211> LENGTH: 15
<212> TYPE: PRT
<213> ORGANISM: Artificial Sequence
<220> FEATURE:
<223> OTHER INFORMATION: Synthetic peptide

<400> SEQUENCE: 61

Met Asp Ile Asp Pro Tyr Lys Glu Phe Gly Ala Ser Val Glu Leu
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic peptide

<400> SEQUENCE: 62

Pro Tyr Lys Glu Phe Gly Ala Ser Val Glu Leu Leu Ser Phe Leu
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic peptide

<400> SEQUENCE: 63

Phe Gly Ala Ser Val Glu Leu Leu Ser Phe Leu Pro Ser Asp Phe
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Synthetic peptide

<400> SEQUENCE: 64

Val Glu Leu Leu Ser Phe Leu Pro Ser Asp Phe Phe Pro Ser Ile
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic peptide

<400> SEQUENCE: 65

Ser Phe Leu Pro Ser Asp Phe Phe Pro Ser Ile Arg Asp Leu Leu
1               5                   10                  15
```

```
<210> SEQ ID NO 66
<211> LENGTH: 15
<212> TYPE: PRT
<213> ORGANISM: Artificial Sequence
<220> FEATURE:
<223> OTHER INFORMATION: Synthetic peptide

<400> SEQUENCE: 66

Ser Asp Phe Phe Pro Ser Ile Arg Asp Leu Leu Asp Thr Ala Ser
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic peptide

<400> SEQUENCE: 67

Pro Ser Ile Arg Asp Leu Leu Asp Thr Ala Ser Ala Leu Tyr Arg
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic peptide

<400> SEQUENCE: 68

Asp Leu Leu Asp Thr Ala Ser Ala Leu Tyr Arg Glu Ala Leu Glu
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Synthetic peptide

<400> SEQUENCE: 69

Thr Ala Ser Ala Leu Tyr Arg Glu Ala Leu Glu Ser Pro Glu His
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Synthetic peptide

<400> SEQUENCE: 70

Leu Tyr Arg Glu Ala Leu Glu Ser Pro Glu His Cys Ser Pro His
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic peptide

<400> SEQUENCE: 71

Ala Leu Glu Ser Pro Glu His Cys Ser Pro His His Thr Ala Leu
1               5                   10                  15

<210> SEQ ID NO 72
```

```
<211> LENGTH: 15
<212> TYPE: PRT
<213> ORGANISM: Artificial Sequence
<220> FEATURE:
<223> OTHER INFORMATION: Synthetic peptide

<400> SEQUENCE: 72

Pro Glu His Cys Ser Pro His His Thr Ala Leu Arg Gln Ala Ile
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Synthetic peptide

<400> SEQUENCE: 73

Ser Pro His His Thr Ala Leu Arg Gln Ala Ile Leu Cys Trp Gly
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Synthetic peptide

<400> SEQUENCE: 74

Thr Ala Leu Arg Gln Ala Ile Leu Cys Trp Gly Glu Leu Met Asn
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Synthetic peptide

<400> SEQUENCE: 75

Gln Ala Ile Leu Cys Trp Gly Glu Leu Met Asn Leu Ala Thr Trp
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Synthetic peptide

<400> SEQUENCE: 76

Cys Trp Gly Glu Leu Met Asn Leu Ala Thr Trp Val Gly Ser Asn
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Synthetic peptide

<400> SEQUENCE: 77

Leu Met Asn Leu Ala Thr Trp Val Gly Ser Asn Leu Glu Asp Pro
1               5                   10                  15

<210> SEQ ID NO 78
<211> LENGTH: 15
```

<212> TYPE: PRT
<213> ORGANISM: Artificial Sequence
<220> FEATURE:
<223> OTHER INFORMATION: Synthetic peptide

<400> SEQUENCE: 78

Ala Thr Trp Val Gly Ser Asn Leu Glu Asp Pro Ala Ser Arg Glu
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Synthetic peptide

<400> SEQUENCE: 79

Gly Ser Asn Leu Glu Asp Pro Ala Ser Arg Glu Leu Val Val Ser
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Synthetic peptide

<400> SEQUENCE: 80

Glu Asp Pro Ala Ser Arg Glu Leu Val Val Ser Tyr Val Asn Val
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Synthetic peptide

<400> SEQUENCE: 81

Ser Arg Glu Leu Val Val Ser Tyr Val Asn Val Asn Met Gly Leu
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Synthetic peptide

<400> SEQUENCE: 82

Val Val Ser Tyr Val Asn Val Asn Met Gly Leu Lys Ile Arg Gln
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Synthetic peptide

<400> SEQUENCE: 83

Val Asn Val Asn Met Gly Leu Lys Ile Arg Gln Leu Leu Trp Phe
1               5                   10                  15

<210> SEQ ID NO 84
<211> LENGTH: 15
<212> TYPE: PRT

```
<213> ORGANISM: Artificial Sequence
<220> FEATURE:
<223> OTHER INFORMATION: Synthetic peptide

<400> SEQUENCE: 84

Met Gly Leu Lys Ile Arg Gln Leu Leu Trp Phe His Ile Ser Cys
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic peptide

<400> SEQUENCE: 85

Ile Arg Gln Leu Leu Trp Phe His Ile Ser Cys Leu Thr Phe Gly
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Synthetic peptide

<400> SEQUENCE: 86

Leu Trp Phe His Ile Ser Cys Leu Thr Phe Gly Arg Glu Thr Val
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Synthetic peptide

<400> SEQUENCE: 87

Ile Ser Cys Leu Thr Phe Gly Arg Glu Thr Val Leu Glu Tyr Leu
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Synthetic peptide

<400> SEQUENCE: 88

Thr Phe Gly Arg Glu Thr Val Leu Glu Tyr Leu Val Ser Phe Gly
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Synthetic peptide

<400> SEQUENCE: 89

Glu Thr Val Leu Glu Tyr Leu Val Ser Phe Gly Val Trp Ile Arg
1               5                   10                  15

<210> SEQ ID NO 90
<211> LENGTH: 15
<212> TYPE: PRT
<213> ORGANISM: Artificial Sequence
```

```
<220> FEATURE:
<223> OTHER INFORMATION: Synthetic peptide

<400> SEQUENCE: 90

Glu Tyr Leu Val Ser Phe Gly Val Trp Ile Arg Thr Pro Pro Ala
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Synthetic peptide

<400> SEQUENCE: 91

Ser Phe Gly Val Trp Ile Arg Thr Pro Pro Ala Tyr Arg Pro Pro
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Synthetic peptide

<400> SEQUENCE: 92

Trp Ile Arg Thr Pro Pro Ala Tyr Arg Pro Pro Asn Ala Pro Ile
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Synthetic peptide

<400> SEQUENCE: 93

Pro Pro Ala Tyr Arg Pro Pro Asn Ala Pro Ile Leu Ser Thr Leu
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Synthetic peptide

<400> SEQUENCE: 94

Arg Pro Pro Asn Ala Pro Ile Leu Ser Thr Leu Pro Glu Thr Thr
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Synthetic peptide

<400> SEQUENCE: 95

Ala Pro Ile Leu Ser Thr Leu Pro Glu Thr Thr Val Val Arg Arg
1               5                   10                  15

<210> SEQ ID NO 96
<211> LENGTH: 15
<212> TYPE: PRT
<213> ORGANISM: Artificial Sequence
<220> FEATURE:
```

<223> OTHER INFORMATION: Synthetic peptide

<400> SEQUENCE: 96

Ser Thr Leu Pro Glu Thr Thr Val Val Arg Arg Arg Gly Arg Ser
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Synthetic peptide

<400> SEQUENCE: 97

Glu Thr Thr Val Val Arg Arg Arg Gly Arg Ser Pro Arg Arg Arg
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Synthetic peptide

<400> SEQUENCE: 98

Val Arg Arg Arg Gly Arg Ser Pro Arg Arg Arg Thr Pro Ser Pro
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Synthetic peptide

<400> SEQUENCE: 99

Gly Arg Ser Pro Arg Arg Arg Thr Pro Ser Pro Arg Arg Arg Arg
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Synthetic peptide

<400> SEQUENCE: 100

Arg Arg Arg Thr Pro Ser Pro Arg Arg Arg Ser Gln Ser Pro
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Synthetic peptide

<400> SEQUENCE: 101

Pro Ser Pro Arg Arg Arg Arg Ser Gln Ser Pro Arg Arg Arg Arg
1               5                   10                  15

<210> SEQ ID NO 102
<211> LENGTH: 15
<212> TYPE: PRT
<213> ORGANISM: Artificial sequence
<220> FEATURE:
<223> OTHER INFORMATION: Synthetic peptide

```
<400> SEQUENCE: 102

Arg Arg Arg Ser Gln Ser Pro Arg Arg Arg Ser Gln Ser Arg
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Synthetic peptide

<400> SEQUENCE: 103

Gln Ser Pro Arg Arg Arg Ser Gln Ser Arg Glu Ser Gln Cys
1               5                   10                  15
```

HEPATITIS B VACCINE

This application is a national phase application under 35 U.S.C. § 371 of International Application No. PCT/CN2014/072570, filed Feb. 26, 2014, which claims benefit of priority to Chinese Patent Application No. 201310080863.X, filed Mar. 13, 2013. The entire contents of the above-referenced disclosures are specifically incorporated herein by reference.

Pursuant to 37 C.F.R. 1.821(c), a sequence listing is submitted herewith as an ASCII compliant text file named "UNITP0009US_ST25.txt", created on Sep. 8, 2015 and having a size of ~27 kilobytes. The content of the aforementioned file is hereby incorporated by reference in its entirety.

FIELD OF THE INVENTION

The present invention relates to a type of hepatitis B vaccine, in particular, relates to a hepatitis B vaccine, comprising HBsAg, HBcAg and phosphorothioate oligodeoxynucleotide with the immunostimulatory activity.

BACKGROUND OF THE INVENTION

Hepatitis B virus (HBV) infection is a serious public health problem worldwide. HBV infection is an important cause of chronic hepatitis B, cirrhosis and hepatocellular carcinoma (Fattovich G. J Hepatol 2008; 48: 335-352). Clinically, the treatment of chronic HBV infection mainly relies on the common drugs nucleoside analogues and interferons. Nucleoside analogs cannot completely remove cccDNA in liver cells, and a long-term use of them may lead to occurrence of drug-resistant mutants and rebounding after drug discontinuance (Kwon H, Lok A S Nat Rev Gastroenterol Hepatol 2011; 8: 275-284). Interferon is not suitable for asymptomatic HBV carriers. Among patients with chronic HBV, the HBeAg seroconversion rate after use for half a year is only 33%, moreover, the interferon has high side effect, which also restricts its applications (Tang S X, Yu G L. Lancet 1990; 335 (8684): 302).

At present, the widely used hepatitis B protein vaccine can produce protective antibodies by inducing humoral immunity, to achieve the goal of prevention. A large number of studies have shown that protective antibodies can only eliminate the extracellular virus particles. The elimination of the intracellularly infected virus mainly relies on specific cellular immune response, helper T cells, IFN-γ and other Th1-type cell factors producing from $CD4^+$ T cells, in particular virus-specific cytotoxic T lymphocytes (CTL) (Chin R, Lacamini S. Rev Med Viorl 2003: 13 (4): 255-72). The cellular immune response will directly affect the prognosis of hepatitis B. Therefore, an ideal hepatitis B vaccine should induce the specific humoral and cellular immunity, to break through immune tolerance of hepatitis B.

Currently, the research and development of therapeutic vaccines for hepatitis B focus on HBsAg. Through overcoming the immune tolerance and producing anti-HBsAg antibodies, it can achieve the effect of immune clearance, for example, HBsAg-immunoglobulin complexes by Wen Yumei (Xu D Z, Zhao K, et al. *PLoS ONE*, 2008, 3: e2565), high-dose HBsAg vaccine by Zhang Yijun (Zeng Ying, Zhang Yijun, et al, *Guangdong Medical Journal*, Issue 7, Volume 24, 2003, P740-706) are based on this principle. But the therapeutic effect of the two vaccines is still unclear according to the latest clinical data.

Studies have shown that the subtype of anti-HBsAg antibody for patients with chronic hepatitis B infection is mainly IgG4, while the subtype of anti-HBsAg antibody for patients with cure of hepatitis B infection is mainly IgG1 (≥IgG4), suggesting that Th1 type IgG1 antibody subtype plays an important role in the process of clearing hepatitis B infection. The evaluation on Th1 type antibody subtype higher or lower than Th2 type antibody subtype can prompt the curative effect of hepatitis B (S. Rath, et al. *Clin. exp. Immunol.* (1988) 72, 164-167). Meanwhile, the anti-HBcAg antibody subtype for patients with hepatitis B infection is IgG1>IgG3>IgG4, but for the patients with cure of hepatitis B infection, it is converted to IgG3>IgG1>IgG4, suggesting that the conversion of anti-HBcAg, especially the conversion of anti-HBcAg antibody subtype is possibly closed related to the treatment of hepatitis B (Chien-Fu Huang, et al *Cellular & Molecular Immunology* 2006; 3 (2): 97-106).

In addition, studies have shown that the expression of dendritic cells (pDC) surface receptor TLR9 is down regulated for chronic HBV carriers and patients with chronic hepatitis B, which leads to the body's immune tolerance to HBsAg and unable to produce hepatitis B surface antibody or cellular immunity against HBsAg (Q. Xie et al. Microbes and Infection 11 (2009) 515-523).

In the U.S. Pat. No. 4,547,367, HBcAg particle was used to treat/prevent HBV infection and HBV-mediated diseases. The immunization of chimpanzees using HBcAg particles can protect chimpanzees from HBV infection. Besides, the immunization of newborns produced by hepatitis B carrier mothers using HBcAg particle and HBsAg particle could produce high-titer anti-HBsAg and anti-HBcAg antibody, and no HBV infection was found in the 18-month monitoring. But this patent did not provide the evidences for the conversion of anti-HBcAg antibody subtype, nor provide the the direct evidences for the treatment of HBV infection and HBV-mediated diseases.

In the patent WO2007/031334, the components of hepatitis B therapeutic vaccine were protected, including HBsAg, HBcAg and one kind of saponin adjuvant. CpG-ODN can be used as a common adjuvant, but the hepatitis B therapeutic vaccine should be used in combination with nucleoside analogues for combined treatment, to break through immune tolerance to hepatitis B and the e antigen negative-conversion rate was only 25%.

SUMMARY OF THE INVENTION

The present invention relates to a pharmaceutical composition, comprising: i) HBsAg, ii) HBcAg, iii) CpG-ODN, and/or optionally iv) a pharmaceutically acceptable carrier. In particular, the pharmaceutical composition in the present invention can be used as a prophylactic or therapeutic vaccine. In some embodiments, the said pharmaceutical composition comprises the above components i)-iii) and optionally iv).

In some embodiments in the present invention, the said HBsAg has the sequence as shown in SEQ ID NO:1.

In other embodiments in the present invention, said HBcAg has the sequence as shown in SEQ ID NO:2.

In further embodiments of the present invention, said CpG-ODN includes phosphothioate linkage. In particular, said CpG-ODN is phosphorothioate oligodeoxynucleotide, preferably phosphorothioate oligodeoxynucleotide.

In further embodiments of the present invention, said CpG-ODN contains two or more 5'-NTCGTT-3' motif.

In further embodiments of the present invention, the length of said CpG-ODN is 15~35 nucleotides, preferably 20~25 nucleotides.

In further embodiments of the present invention, the said CpG-ODN sequence is selected from the following: 5'-TCG TTC GTT CGT TCG TTC GTT-3' (SEQ ID NO: 3), 5'-TCG TTC GTT CGT TCG TTC GTT CGT T-3' (SEQ ID NO: 4), 5'-TCG TCG TCG TCG TCG TCG TCG-3' (SEQ ID NO: 5) and 5'-TCC ATG ACG TTC CTG ACG TT-3' (SEQ ID NO: 6), preferably the said CpG-ODN has the sequence: 5'-TCG TTC GTT CGT TCG TTC GTT-3'.

In further embodiments of the present invention, the range of the relative weight ratio of the components i), ii) and iii) in the pharmaceutical composition is 1:0.2~5:1~50, preferably 1:1~5:2~15.

The present invention also relates to a hepatitis B vaccine, comprising i) HBsAg, ii) HBcAg, iii) CpG-ODN, and optionally iv) a pharmaceutically acceptable carrier.

The present invention also relates to a kit, comprising a pharmaceutical composition or hepatitis B vaccine according to the present invention and optionally instructions for use thereof.

In one aspect, the present invention relates to the uses of pharmaceutical composition in the manufacture of the medicament for treating HBV infection and/or HBV-mediated diseases, preferably the HBV infection and/or HBV-mediated diseases are selected from hepatitis B, cirrhosis and liver cancer.

In another aspect, the present invention relates to the use of the pharmaceutical composition in the manufacture of the medicament that generate immune response against HBV (preferably, inducing Th1 and Th2-type immune response).

In another aspect, the present invention relates to the uses of the pharmaceutical composition in the manufacture of the medicament that convert the anti-HBcAg antibody subtype.

In yet another aspect, the present invention relates to the uses of pharmaceutical composition in the manufacture of the medicament that break through the HBV immune tolerance.

In yet another aspect, the present invention relates to the uses of pharmaceutical composition in the manufacture of the medicament that realize the HBsAg Th1/Th2 balance of the immune response (e.g. roughly inducing Th1 and Th2-type immune response).

In yet another aspect, the present invention relates to a pharmaceutical composition, comprising: i) HBsAg, ii) HBcAg, and iii) CpG-ODN. In particular, the pharmaceutical compositions in the present invention can be used for the treatment of HBV infection and/or HBV-mediated diseases, for the generating immune response against HBV (preferably, inducing Th1 and Th2-type immune response) in subjects, for the conversion of subtype of anti-HBcAg antibody, for inducing the antigen-specific CTL killing activity and/or for breaking through HBV immune tolerance in subjects.

In yet another aspect, the present invention relates to a method for treating HBV infection and/or HBV-mediated disease, including applying the therapeutically effective dose of pharmaceutical composition in the subjects.

In yet another aspect, the present invention relates to a method of generating an immune response against HBV (preferably inducing Th1 and Th2-type immune response), including applying the therapeutically effective dose of pharmaceutical composition in the subjects.

In yet another aspect, the present invention relates to a method that converts the subtype of anti-HBcAg antibody in the subjects, including applying the therapeutically effective dose of pharmaceutical composition in the subjects.

In yet another aspect, the present invention relates to a method that breaks through HBV immune tolerance in subjects, including applying the therapeutically effective dose of pharmaceutical composition in the subjects.

In yet another aspect, the present invention relates to a method that induces antigen-specific CTL killing activity in the subjects, including applying the therapeutically effective dose of pharmaceutical composition in the subjects.

In yet another aspect, the present invention relates to a method that realizes HBsAg Th1/Th2 balance of the immune response in the subjects (e.g. roughly inducing Th1 and Th2-type immune response), including applying the therapeutically effective dose of pharmaceutical composition in the subjects.

In some embodiments, the pharmaceutical compositions of the present invention do not contain saponin adjuvant.

DETAILED EMBODIMENTS

Figure 1:
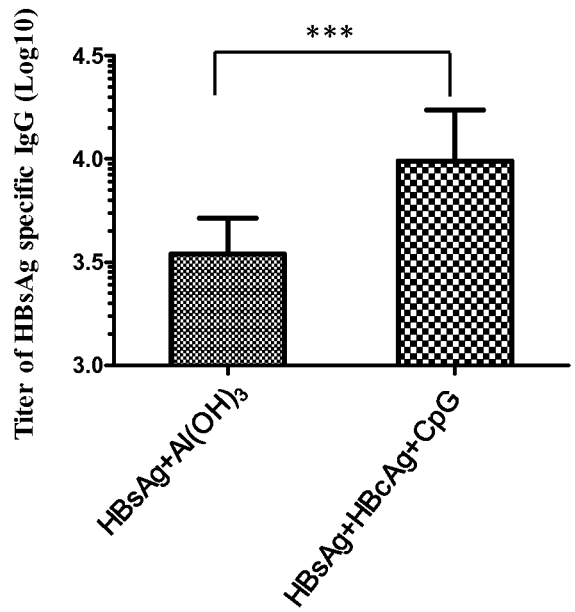
FIG. 1 shows that the composition of the present invention enhances the immune response of mice on hepatitis B surface antigen (HbsAg) specific total IgG when compared with the conventional vaccine components.

The invention is described herein in connection with drawings and certain specific embodiments. However, to the extent that the following detailed description is specific to a particular embodiment or a particular use, such is intended to be illustrative only and is not to be construed as limiting the scope of the invention.

One of the objects of the present invention is to overcome the known deficiencies of drugs used for treating hepatitis B infection in the prior arts.

In particular, an object of the present invention is to provide a pharmaceutical composition which can produce strong immune response in patients with chronic HBV infection, promote the differentiation of anti-HBsAg-IgG2a antibody subtypes and IgG2a and IgG1 tend to the balance; and induce the conversion of subtypes of anti-HBcAg antibodies and/or break through the immune tolerance in patients with HBV infection.

Another object of the present invention is to provide the uses of the pharmaceutical composition in the treatment of HBV infection and/or HBV-mediated diseases, and the method for treating HBV infection and/or HBV-mediated diseases.

To achieve the above objects, the present invention provides a pharmaceutical composition, comprising:

i) HBsAg, antigen fragments, variants of the antigen, or a mixture of at least two of them, ii) HBcAg, the antigen fragments, variants of the antigen or the antigen fragment, or a mixture of at least two of them, iii) CpG-ODN, which is fully phosphorothioate oligonucleotide, whose sequence having two or more copies of 5'-NTCGTT-3' motif, and 20~25 bases in the length. Preferably the oligonucleotide is selected from the following base sequences: 5'-TCG TTC GTT CGT TCG TTC GTT-3', 5'-TCG TTC GTT CGT TCG TTC GTT CGT T-3', 5'-TCG TCG TCG TCG TCG TCG TCG-3' or 5'-TCC ATG ACG TTC CTG ACG TT-3', more preferably 5'-TCG TTC GTT CGT TCG TTC GTT-3'.

The composition of the present invention has achieved an unexpected technical effect. Compared with the existing commercially available hepatitis B vaccines, it can mediate a stronger immune response in the in vivo tests in mice, including anti-HBsAg antibody, anti-HBcAg antibody, anti-adr serotype neutralizing antibodies, in particular medicate the Th1 cellular immune response, produce cytokines IFN-γ associated with viral clearance, promote the differentiation and maturation of anti-HBs-IgG2a antibody subtypes and the conversion of anti-HBcAg antibody subtypes, to achieve a balance of humoral immunity and cellular immunity.

The composition HBsAg+CpG is disclosed in prior arts (refer to the Patent CN101492672). The inventors of the present invention have surprisingly found that the pharmaceutical composition of the present invention (the composition of HBcAg, HBsAg and CpG ODN) can produce anti-HBsAg specific antibody significantly better than HBsAg+CpG composition, exhibiting surprising synergistic effect.

More surprisingly, in vivo test in transgenic mice showed that, the composition according to the present invention can break through the immune tolerance of transgenic mice, produce high titer of anti-HBsAg antibody, anti-HBcAg antibody, neutralizing antibody, mediate Th1 cellular immune response, promote the differentiation and maturation of IgG2a antibody subtypes. At the same time, the detection on the expression level of serum hepatitis B surface antigen showed that, multiple immunizations of the composition in the present invention could significantly eliminate the HBV in the transgenic mice, to decrease the expression level of hepatitis B virus. The compositions in the invention also exhibited strong in vivo killing activity of inducing strong antigen-specific cytotoxic T lymphocytes (CTL), in particular, the in vivo killing activity of HBsAg CTL and HBcAg CTL. The experiment further confirmed that the composition in the present invention is far better than the existing vaccines in the prior arts and more effective for treating hepatitis B (especially chronic hepatitis B).

In addition, BALB/c mice and model mice can mediate strong anti-HBcAg immune response and achieve the conversion of anti-HBcAg antibody subtypes, that is, the IgG2a antibody level is higher than that of IgG1, which is consistent with the relationship of antibody subtype of cured patients with hepatitis B infection. This encouraging result showed that the composition according to the present invention can be used as therapeutic vaccine of hepatitis B, to solve the problem that has plagued people for a long time.

Definitions

Unless otherwise defined, all technical terms used herein shall have the same meaning for the ordinary technicians in the field. For the terms and definitions in the field, professionals can refer to Current Protocols in Molecular Biology (Ausubel). The abbreviations of amino acid residues are the standard 3-letter and/or 1-letter code that represents 20 commonly used L-amino acids.

Although the numerical ranges and parameters approximations are indicated in the broad sense in the present invention, the numerical values described in specific embodiments should be recited as accurate as possible. However, any value has some errors, which is caused by the standard deviation in the measurement. In addition, all ranges disclosed herein should be understood to cover any and all sub-ranges. For example, the range "1 to 10" as recorded should be understood to include any and all sub-ranges between the minimum 1 and the maximum 10 (inclusive), i.e. all sub-ranges starting from minimum 1 or a larger value, e.g. from 1 to 6.1, and the sub-ranges ended by maximum 10 or a smaller value, e.g. from 5.5 to 10. Further, any references that are "incorporated herein" should be understood to be incorporated as a whole.

Furthermore, it should be noted that, the singular form used herein shall include its plural form of the object, unless limited to an object clearly and unambiguously. The term "or" can be exchanged with the term "and/or", unless otherwise clearly indicated.

The term "polypeptide" as used herein refers to a polymer of amino acids, and no restriction on the number of amino acids, thus, it includes peptides, oligopeptides, dimers, trimers, oligomers and particles, etc. Furthermore, the term "polypeptide" not only includes the pure amino acid polymer obtained after the translation in the ribosome, but also includes the polypeptide obtained after post-translational modifications (e.g., glycosylation, acetylation, phosphorylation, thio, etc.).

As used herein, the term "antigenic fragment" refers to a natural or synthetic polypeptide fragment, which retains the antigenic property of natural or synthetic polypeptides, i.e. capable of inducing an immune response against the natural or synthetic polypeptide.

The term "HBsAg, HBs" as used herein covers naive HBsAg, HBsAg antigenic fragments, HBsAg functional variants and any combination thereof, in particular, the naive HBsAg is naive HBsAg polypeptide containing 226 amino acids. More particularly, the HBsAg is from the existing known naive HBsAg polypeptides with standard HBV genotypes A, B, C, D, E, F, G and/or H. In some embodiments, the HBsAg contains the sequence as shown in SEQ ID NO: 1.

The term "HBsAg antigenic fragment" as used herein refers to the following polypeptides, i.e. the polypeptide has continuous or discontinuous fragments less than 226 amino acids in naive HBsAg and the polypeptide retains the antigenicity of naive HBsAg.

The term "HBsAg functional variant" used herein refers to the following polypeptides, i.e., the polypeptide has a most 30, at most 25, at most 20, at most 15, at most 10, at most 5, at most 4, at most 3, at most 2 or at most 1 amino acid deletion, insertion, addition or replacement compared with the naive HBsAg or HBsAg segments, and the polypeptide retains the function of naive HBsAg (e.g. antigenicity).

As used herein, the term "hepatitis B core antigen (HBcAg, HBc)" refers to naïve HBcAg, HBcAg antigenic fragments, HBcAg functional variants and any combination thereof. In particular, the naïve HBcAg is naïve HBcAg polypeptides containing 183 amino acids. More particularly, the naïve HBcAg is derived from the existing known naïve HBcAg of standard HBV genotypes A B, C, D, E, F, G, and/or H. In some embodiments, HBcAg is from $HBcAg_{1-x}$ polypeptide, which represents amino acid fragments at the positions 1-X of naïve HBcAg, in particular, X is 149-183. In other embodiments, the naïve HBcAg is selected from the polypeptides having the following sequence: amino acids at position 1-149 in SEQ ID NO: 2, amino acids at position 1-150 in SEQ ID NO: 2, amino acids at position 1-151 in SEQ ID NO: 2, amino acids at position 1-152 in SEQ ID NO: 2, amino acids at position 1-153 in SEQ ID NO: 2, amino acids at position 1-154 in SEQ ID NO: 2, amino acids at position 1-155 in SEQ ID NO: 2, amino acids at position 1-156 in SEQ ID NO: 2, amino acids at position 1-157 in SEQ ID NO: 2, amino acids at position 1-158 in SEQ ID NO: 2, amino acids at position 1-159 in SEQ ID NO: 2, amino acids at position 1~160 in SEQ ID NO: 2, amino acids at position 1-161 in SEQ ID NO: 2, amino acids at position 1-162 in SEQ ID NO: 2, amino acids at position 1-163 in SEQ ID NO: 2, amino acids at position 1-164 in SEQ ID NO: 2, amino acids at position 1-165 in SEQ ID NO: 2, amino acids at position 1-166 in SEQ ID NO: 2, amino acids at position 1~167 in SEQ ID NO: 2, amino acids at position 1-168 in SEQ ID NO: 2, amino acids at position 1-169 in SEQ ID NO: 2, amino acids at position 1-170 in SEQ ID NO: 2, amino acids at position 1-171 in SEQ ID NO: 2, amino acids at position 1-172 in SEQ ID NO: 2, amino acids at position 1-173 in SEQ ID NO: 2, amino acids at position 1~174 in SEQ ID NO: 2, amino acids at position 1-175 in SEQ ID NO: 2, amino acids at position 1-176 in SEQ ID NO: 2, amino acids at position 1-177 in SEQ ID NO: 2, amino acids at position 1-178 in SEQ ID NO: 2, amino acids at position 1-179 in SEQ ID NO: 2, amino acids at position 1-180 in SEQ ID NO: 2, amino acids at position 1~181 in SEQ ID NO: 2, amino acids at position 1-182 in SEQ ID NO: 2, amino acids at position 1-183 in SEQ ID NO: 2. In some embodiments, the HBcAg has the sequences indicated in SEQ ID NO: 2.

The term "HBcAg antigenic fragment" used herein refers to the following polypeptides, i.e. the polypeptide has the continuous or discontinuous segments of less than 183 amino acids in naïve HBcAg and the polypeptide retains the antigenicity of naïve HBcAg.

The term "HBcAg functional variant" used herein refers to the following polypeptides, i.e., the polypeptide has a most 30, at most 25, at most 20, at most 15, at most 10, at most 5, at most 4, at most 3, at most 2 or at most 1 amino acid deletion, insertion, addition or replacement compared with the naïve HBcAg or HBcAg segments, and the polypeptide retains the function of naïve HBcAg (e.g. antigenicity).

Preferably, in the present invention, HBcAg and HBsAg are present in particulate form in the composition.

As used herein, the term "pharmaceutical composition", "combined drug" and "drug combination" can be interchangeably used, which refers to at least one drug and any pharmaceutically acceptable excipients or combination thereof to achieve a particular purpose. In some embodiments, the pharmaceutical composition comprises the separate combination temporally and/or dimensionally provided that they can act each other to achieve the purpose in the present invention. For example, the compositions contained in the drug combination (e.g. HBsAg, HBcAg and CpG-ODN) can be used in the subjects wholly or separately. When the compositions contained in the drug combination are separately used in subjects, the compositions can be used in subjects simultaneously or sequentially.

The term "CpG oligodeoxynucleotides" or "CpG-ODN" as used herein refers to a short single-stranded synthetic DNA molecule comprising one or more "CpG" units, wherein C is cytosine, G is guanine, p is phosphodiester linkage. In particular, the CpG oligodeoxynucleotide is non-methylated. In some embodiments, the CpG-ODN contains phosphorothioate linkage or phosphorothioate backbone. That is, in some embodiments, the CpG-ODN is phosphorothioate oligodeoxynucleotide (i.e. thio oligodeoxynucleotide). Preferably, all linkages between nucleotides in CpG-ODN are phosphorothioate linkages, i.e., the CpG-ODN is full-thioxo oligodeoxynucleotides. In other embodiments, the CpG-ODN contains two or more 5'-NTCGTT-3'motifs. In still other embodiments, the length of the CpG-ODN is 15 to 35 nucleotides, preferably 20 to 25 nucleotides. In particular, the CpG-ODN sequence is selected from the following: 5'-TCG TTC GTT CGT TCG TTC GTT-3' (SEQ ID NO: 3), 5'-TCG TTC GTT CGT TCG TTC GTT CGT T-3' (SEQ ID NO: 4), 5'-TCG TCG TCG TCG TCG TCG TCG-3' (SEQ ID NO: 5) and 5'-TCC ATG ACG TTC CTG ACG TT-3' (SEQ ID NO: 6), and more particularly, the CpG-ODN has the sequence 5'-TCG TTC GTT CGT TCG TTC GTT-3'.

The term "therapeutically effective dose" or "effective dose" as used herein refers to the dose that is adequate to present its benefits to the subjects applied. The actual dose administered, rate of administration and time-course of administration will depend on the situations and severity of the subjects to be treated. The prescription (e.g., decision on dose, etc) is the responsibility of general practitioner and other physicians who make decisions. Generally considerations should be taken to the disease, condition of individual patient, the site of delivery, route of administration and other known factors for doctors.

The term "HBV-mediated disease" as used herein refers to the diseases that are caused, induced, aggravated by HBV or those whose risk and/or occurrence is associated with HBV, such as HBV carriers, hepatitis B, cirrhosis, liver ascites, liver cancer, etc.

The term "Conversion of anti-HBcAg antibody subtypes" as used herein means that the anti-HBcAg antibody subtype is converted to that consistent with cured patients with hepatitis B, namely, consistent with the antibody subtype of cured patients with HBV infection. In particular, in mice, the anti-HBcAg antibody subtype is converted from IgG1>IgG2a to IgG2a>IgG2b>IgG1 or IgG2b>IgG2a>IgG1, for example, IgG2a>IgG1. In humans, the anti-HBcAg antibody subtype is converted from IgG1>IgG3>IgG4 to IgG3>IgG1>IgG4.

The term "Subject" as used herein refers to a mammal, such as a human, or other animals, such as wild animals (such as herons, storks, cranes, etc.), livestock (such as ducks, geese, etc.) or experimental animals (such as orangutans, monkeys, rats, mice, rabbits, guinea pigs, marmots, ground squirrels, etc.).

Another embodiment of the compositions in the present invention, comprising i) HBsAg or variant thereof, ii) $HBcAg_{1-183}$, and iii) phosphorothioate oligonucleotide CpG-ODN containing 21 bases, whose sequences contain two or more copies of 5'-NTCGTT-3' motifs.

In some embodiments, the ratio of relative weights of components i), ii) and iii) in the pharmaceutical composition in the present invention is 1:0.2~5:1~50, preferably 1:1~5: 2~15, and more preferably 1:1:2.

In other embodiments, the compositions in the present invention may also contain other additives, such as drug carriers or additives, especially when it exists in the form of a pharmaceutical formulation.

In some embodiments, the pharmaceutical compositions in the present invention do not contain saponin adjuvant.

The preferred pharmaceutical carriers are, in particular, water and buffer solution, and preferably the isotonic salt solution are PBS (phosphate buffered saline), dextrose, mannitol, dextrose, lactose, starch, magnesium stearate, cellulose, carbonate magnesium, 0.3% glycerol, hyaluronic acid, ethanol or polyalkylene glycols such as polyethylene glycol, triglycerides, and etc. The types of pharmaceutical carriers particularly rely on whether the compositions in the present invention are administered orally, nasally, intradermally, or subcutaneously, intramuscularly or intravenously. The compositions according to the present invention may contain wetting agents, emulsifying agents or buffer solutions, which are used as additives.

The pharmaceutical compositions, vaccines or pharmaceutical formulations in the present invention can be used through any appropriate approaches, for example, oral, nasal, intradermal, subcutaneous, intramuscular or intravenous administration.

Example 1

The combined HBsAg, HBcAg and CpG-ODN enhanced the immune response of hepatitis B surface antigen-specific total IgG.

In order to detect the immune response of hepatitis B surface total antigen-specific IgG of HBsAg+HBcAg+CpG-ODN composition. The inventor mixed HBsAg, HBcAg and CpG-ODN, HBsAg and $Al(OH)_3$ adjuvant respectively, and immunized the mice with the mixture. By detecting the serum HBsAg-specific IgG level and performing statistical analysis, the effect of combination of HBsAg, HBcAg with CpG-ODN on immune response of HBsAg total IgG was evaluated by comparing with the combination of HBsAg and $Al(OH)_3$.

BALB/c mice were used in this example, female, 6-8 weeks, purchased from SLAC. The HBsAg antigen used in the example was purchased from Prospec (lot number: 1111PHADW22, sequences were shown in SEQ ID NO: 1). It belonged to adw2 subtypes of *Pichia* expression, with purity of over 95%, stored in 4° C. refrigerator for future use. The HBcAg antigen (sequences were shown in SEQ ID NO: 2) was prepared by the inventor. It was a naïve hepatitis B core protein of *E. coli* expression. The purification process can refer to the report in *Chinese Journal of Biologicals* (Li Jilai, Xu Jing et al, Volume 24, 2011, P. 1121-1125). The specific steps were as follows: after collected, the bacteria were re-suspended in 10 mM sodium phosphate buffer, sonicated, centrifuged to fetch the supernatant, then the saturated ammonium sulfate was added to reach the final concentration of 33%; after fully mixed at 4° C. overnight; on the next day, it was centrifuged and the precipitation was re-suspended using 10 mM sodium phosphate buffer, put in a dialysis bags, to dialyze 24 h at 4° C. After dialysis, through hydroxyapatite chromatography, protein peaks were collected, concentrated and purified by Sephacryl S-400 HR gel filtration chromatography, to collect the target protein peaks; and stored in a 4° C. refrigerator for use. The CpG-ODN sequence used in the present example was 5'-TCG TTC GTT CGT TCG TTC GTT-3', with reference to the chemical synthesis preparation method of solid phase phosphoramidite triester method, as described in the patent CN200810004736.0. The method started from 3' end, 1) deprotection: firstly remove nucleotide protecting group DMT (dimethoxytrityl) that connects with CpG, to get free 5' hydroxyl group, for further condensation reaction in the next step; 2) activation: mix the phosphoramidite protected nucleotide monomer and tetrazolium activator to enter the synthesis column, form a tetrazolyl phosphoramidite reactive intermediates, and then this intermediate will have condensation reaction with the deprotected nucleotide; 3) connection: when tetrazolyl phosphoramidite reactive intermediate encountered the deprotected nucleotide on CpG, affinity reaction with the 5'hydroxyl group would happen for condensation and off-tetrazole. At this time, oligonucleotide chain would extend forward one base; 4) oxidation: when condensation reaction occurred, nucleotide monomer connected CpG oligonucleotides through phosphorous ester bond, but the phosphorous ester bond was not stable, easy to be hydrolyzed by acid or base. At this time, phosphoramidite was oxidized to phosphotriester with s-p double bond using thiosulfate reagent, to get stable oligonucleotide; 5) blocking: after the condensation reaction, to prevent the 5'hydroxyl group on CpG that was not involved in reaction from extending in the subsequent reaction cycle, the hydroxyl group at this end was blocked by acetylation. After the above five steps, one deoxynucleotide was connected to CpG nucleotides. The above deprotection, activation, connection, oxidation, and blocking procedures were repeated, to get a DNA fragment crude product; and finally post-synthesis treatment such as cutting, deprotection, purification, quantification was carried out to get the CpG-ODN, and then preserved in a −20° C. refrigerator for standby use.

HBsAg and HBcAg were diluted with PBS (Invitrogen Corporation) to 10 μg/ml; CpG-ODN was diluted to 20

μg/ml with PBS. Al(OH)$_3$ adjuvant was purchased from Beijing Tiantan Biological Products Co., Ltd. The left hind limb gastrocnemius was immunized for BALB/c mice, with injection volume of 100 μl each mouse, 10 mice each group. In the HBsAg+Al(OH)$_3$ group, each mice was injected with 1 μg of HBsAg adsorbed with Al(OH)$_3$. In the HBsAg+ HBcAg+CpG-ODN group, each mouse was injected with 1 μg HBsAg, 1 μg HBcAg and 2 μg CpG-ODN. Mice were immunized once every three weeks, and ten days after second immunization, blood was drawn to separate serum. The serum was diluted with 2% skim milk beginning from 1:30 dilution ratio according to conventional methods, then serially diluted 3-fold for detecting total antigen-specific IgG antibody.

The detection procedure of total antigen-specific IgG antibody was as follows: 96-well microtiter plates (purchased from Nunc) were coated with HBsAg, 25 ng each well, overnight at 4° C. After the plates were washed twice, add the above 3-fold serial dilutions of serum for one hour at 37° C. After the plates were washed three times, add horseradish peroxidase-labeled goat anti-mouse IgG (purchased from SIGMA) at a dilution of 1:30000, 50 μl each well and act 40 min at 37° C. After the plate was washed 3 times, TMB (purchased from Thermo) developing was adopted, 100 μl each well, for development for 15 min. The reaction was terminated by 2M sulfuric acid, 100 μl each well, and the absorbance at 450 nm (OD450 nm) was measured by a microplate reader (calibrated by OD630$_{nm}$), to determine the titer at the end point. The results were shown in FIG. 1.

As shown from FIG. 1, the immune response in the HBsAg+HBcAg+CpG-ODN group was significantly enhanced. The titer of HBsAg specific antibody can reach 4.0 log value. Compared with HBsAg+Al(OH)$_3$, the difference was statistically significant (P<0.001). The titer of the specific antibody can be increased by about three times. The above results showed that, the vaccine of HBsAg+HBcAg+CpG-ODN composition could significantly enhance the immune response of total HbsAg IgG compared with Al(OH)$_3$ adjuvant hepatitis B vaccine.

Example 2

The combined HBsAg, HBcAg and CpG-ODN enhanced the protective antibody level of HBsAg.

The detection on the effect of HBsAb is to monitor whether the hepatitis B vaccine is successfully inoculated. The Hepatitis B vaccine stimulates the immune system to produce HBsAb equivalent to neutralizing antibodies, and its titer was directly associated with the protective effect of vaccines. The production of said antibody showed significant effect on preventing HBV infection. Therefore, the inventor chose the internationally accepted ARCHITECT HBsAb IU Test System (chemiluminescent microparticle immunoassay, CMIA) to detect the concentration of HBsAb (anti-HBsAg) and perform statistical analysis, to evaluate the protective effect of the combination of HBsAg+HBcAg+ CpG-ODN on enhancing the protective antibody level compared with combined HBsAg+Al(OH)$_3$.

In the example, BALB/c mice were used, female, 6-8 weeks, purchased from Shanghai SLAC. The HBsAg, HBcAg, CpG-ODN and Al(OH)$_3$ adjuvant used in this example were as described in example 1.

HBsAg and HBcAg were diluted with PBS to 10 μg/ml; CpG-ODN was diluted to 20 μg/ml with PBS. The left hind limb gastrocnemius was immunized for BALB/c mice, with injection volume of 100 μl each mouse, 10 mice each group. In the HBsAg+Al(OH)$_3$ group, each mice was injected with 1 μg of HBsAg adsorbed with Al(OH)$_3$. In the HBsAg+ HBcAg+CpG-ODN group, each mouse was injected with 1 μg HBsAg, 1 μg HBcAg and 2 μg CpG-ODN. Mice were immunized once every three weeks, and ten days after second immunization, blood was drawn to separate serum. The serum was mixed according to original fold or individual blood was diluted by PBS solution (for 250<IU<1000,500-fold dilution of individual blood sample, and for IU>1000, 5000-fold dilution of individual blood sample), and delivered to the Second Affiliated Hospital of Southeast University for testing. The serum HBsAb (ABBOTT, ARCHITECT system testing) in the immunized mice was detected using ARCHITECT HBsAb IU Test System (chemiluminescent microparticle immunoassay, CMIA). The results were shown in FIG. 2.

Figure 2:
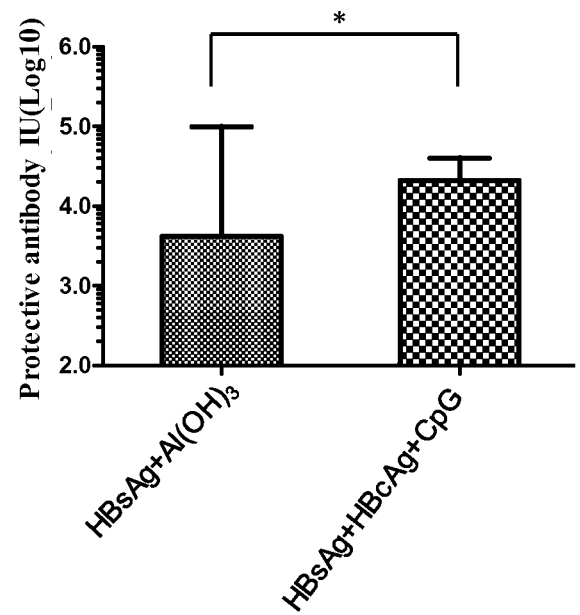
FIG. 2 shows that the composition in the present invention enhances mice to generate the protective antibody immune response when compared with the conventional vaccine components.

As shown from FIG. 2, the level of protective antibody in the HBsAg+HBcAg+CpG-ODN group was significantly enhanced. The titer of specific protective antibody can reach 4.3 log value. Compared with HBsAg+Al(OH)$_3$, the difference was statistically significant (P<0.05). The titer of specific protective antibody can be increased by about five times. The above results showed that, the vaccine of HBsAg+HBcAg+CpG-ODN composition could significantly enhance the level of HBsAg protective antibody, and enhance the protective effect of vaccine compared with Al(OH)$_3$ adjuvant hepatitis B vaccine.

Example 3

The combined HBsAg, HBcAg and CpG-ODN enhanced the immune response of HBsAg Th2 in the humoral immune level.

Figure 3:
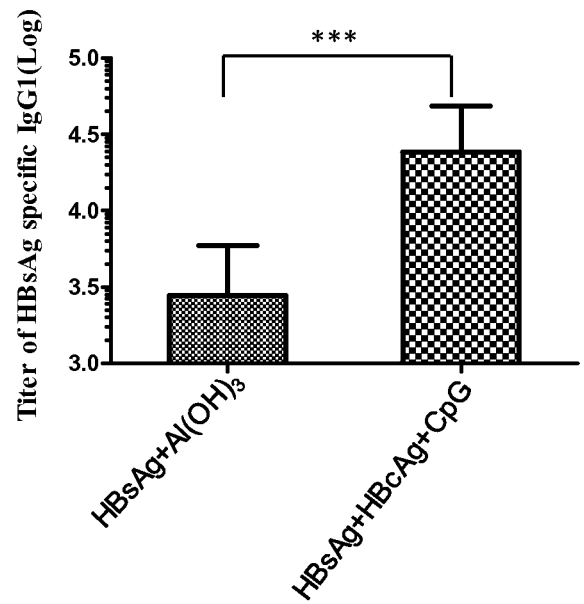
FIG. 3 shows that the composition of the present invention enhances HbsAg Th2 immune response in the humoral immunity level when compared with the conventional vaccine components.

The effect of HBsAg+HBcAg+CpG-ODN composition on Th2 type immune response was determined according to the method described in Example 1. The difference was that the enzyme-labeled antibody used was HRP-labeled goat anti-mouse IgG1 (purchased from SouthernBiotech), with the dilution factor of 1:20000. The results were shown in FIG. 3.

The antigen-specific immune response is divided into two types: Th1 and Th2. The Th2 type of response was associated with high-level of antigen-specific IgG1 antibody titer. Al(OH)$_3$ is an extremely strong Th2 type vaccine adjuvant, which can inhibit Th1 type immune response, induce the high-level specific IgG1 antibody after immunization. In the Example, the IgG1 antibody level producing from the HBsAg+HBcAg+CpG-ODN composition was significantly higher than that in the HBsAg+Al(OH)$_3$ group (P<0.001). The titer of HBsAg-specific IgG1 antibody could increase by nearly 10 times. The above results showed that, the compositions of the present invention could produce a HBsAg-specific IgG1 antibody stronger than Al(OH)$_3$ adjuvant group, to enhance the HBsAg Th2 immune response.

Example 4

The combined HBsAg, HBcAg and CpG-ODN enhanced the immune response of HBsAg Th1 in the humoral immune level.

Figure 4:
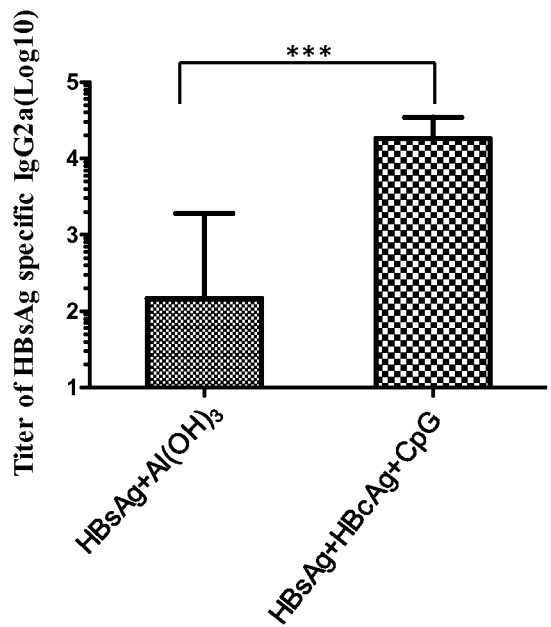
FIG. 4 shows that the composition of the present invention enhances HbsAg Th1 immune response in the humoral immunity level when compared with the conventional vaccine components.

The effect of HBsAg+HBcAg+CpG-ODN composition on Th1 type immune response was determined according to the method described in Example 1. The difference was that the enzyme-labeled antibody used was HRP-labeled goat anti-mouse IgG2a (purchased from SouthernBiotech), with the dilution factor of 1:6000. The results were shown in FIG. 4.

As described in Example 3, Al(OH)$_3$ is an extremely strong Th2 type vaccine adjuvant, which can inhibit Th1 type immune response, induce extremely low level of specific IgG2a antibody after immunization. In the Example, the titer of specific IgG2a antibody induced by Al(OH)$_3$ as the HBsAg adjuvant was only 2.17 log values. When immunization with the HBsAg+HBcAg+CpG-ODN composition in the present invention, the titer of HBsAg specific IgG2a antibody was increased by 2 log value, i.e. 100-folds. The results showed that, the combined HBsAg+HBcAg+CpG-ODN in the present invention extremely stimulated the Th1 immune response against HBsAg.

Example 5

The combined HBsAg, HBcAg and CpG-ODN promoted the Th1/Th2 immune response balance of HBsAg in the humoral immune level.

Figure 5:
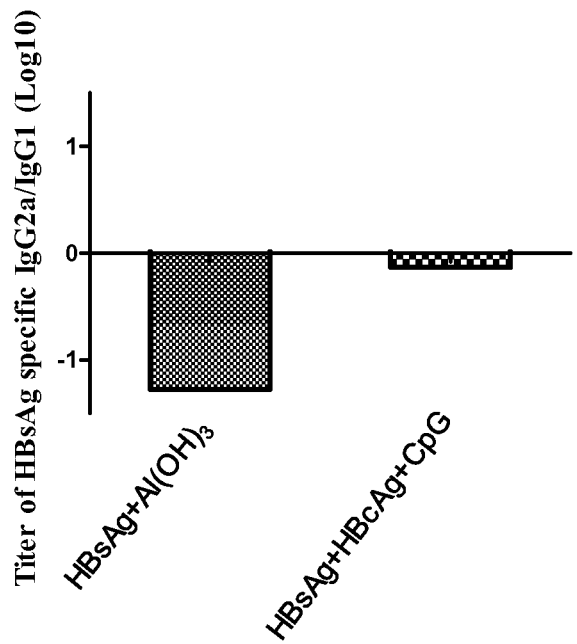
FIG. 5 shows that the composition of the present invention promotes HbsAg Th1/Th2 immune response balance in the humoral immunity level when compared with the conventional vaccine components.

As described in Example 3 and Example 4, the HBsAg+HBcAg+CpG-ODN in the present invention would not only produce high-level of Th2 type immune response on mice, but also produce extremely high level of Th1 type immune response. Th1 promoted CTL response, that is the cell-mediated immunity tendency, while Th2 promoted the production of antibody, that is the cell-mediated immunity tendency. One of the purposes of HBV therapeutic vaccine is to clear away the HBsAg antigen in the serum, to produce effective protective antibodies, mainly humoral immunity playing a role; and the other purpose is to kill the target cells infected with HBV, that is, CTL response, which requires cell-mediated immunity. Thus, both Th1 and Th2 immune responses are very important. In order to directly illustrate the Ti or Th2 response tendency generating from HBsAg+HBcAg+CpG-ODN composition and HBsAg+Al(OH)$_3$ control group, the antigen-specific IgG2a/IgG1 titer ratio (Log 10) would be analyzed and results were shown in FIG. 5. If the ratio was less than 0, it indicated that immune response tended to Th2, and if greater than 0, indicating tended to Th1, and if close to 0, indicating immune response balance. The analysis results showed that, the immune response in the control group (Al(OH)$_3$ as the HBsAg adjuvant) was mainly IgG1, tending to Th2 response; while in the HBsAg+HBcAg+CpG-ODN composition, the specific IgG1 was equivalent to IgG2a, the immune response tended to Th1/Th2 balance.

Example 6

The combined HBsAg, HBcAg and CpG-ODN produced anti-HBcAg antibody subtype IgG2a>IgG1.

Figure 6:
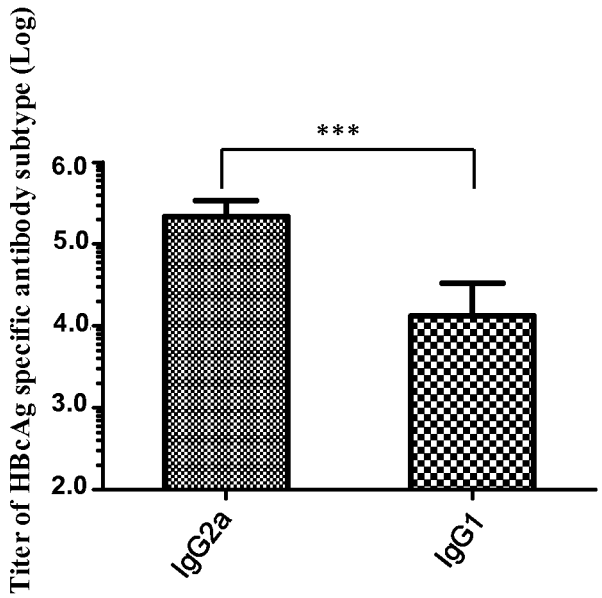
FIG. 6 shows that the anti-HBcAg antibody subtype of the composition of the present invention is IgG2a>IgG1.

The anti-HBcAg antibody subtypes of cured patients with hepatitis B infection were shown as IgG3>IgG1>IgG4. The corresponding antibody subtypes in mice were shown as IgG2a>IgG2b>IgG1 or IgG2b>IgG2a>IgG1. The titers of HBsAg+HBcAg+CpG-ODN composition on mouse anti-HBcAg subtype IgG2a and IgG1 antibody were determined using the method described in Example 3 and Example 4, to investigate whether the composition can promote the conversion of mouse anti-HBcAg antibody subtype to IgG2a>IgG1. The difference was that the coating antigen used for testing was 1 μg/ml HBcAg. Results were shown in FIG. 6. The results showed that, the anti-HBcAg antibody subtype IgG2a produced by HBsAg+HBcAg+CpG-ODN composition herein was more than IgG1, showing significant difference (P<0.001). It suggested that the composition could promote the conversion of mouse anti-HBcAg antibody subtype to the antibody subtype of cured patients with hepatitis B infection.

Example 7

The combined HBsAg, HBcAg and CpG-ODN significantly promoted the HBsAg CTL epitope-specific Th1 cell differentiation and inhibition of Th2 cell proliferation.

In order to clarify the function of HBsAg+HBcAg+CpG-ODN composition in the cell-mediated immunity, the inventor mixed HBsAg, HBcAg and CpG-ODN, HBsAg and Al(OH)$_3$ respectively to immunize mice. Through detection on the IFN-γ and IL-4 secretion level after HBsAg CTL epitope-specific stimulation in spleen cells of immunized mice and statistical analysis, the effect of combined HBsAg HBcAg, with CpG-ODN on promoting antigen-specific Th1 cell differentiation was evaluated compared with combined HBsAg and Al(OH)$_3$.

In the example, BALB/c mice were used, female, 6-8 weeks, purchased from Shanghai SLAC. The HBsAg, HBcAg, CpG-ODN and Al(OH)$_3$ adjuvant used in this example were as described in example 1.

HBsAg and HBcAg were diluted with PBS to 10 μg/ml; CpG-ODN was diluted to 20 μg/ml with PBS. The left hind limb gastrocnemius was immunized for BALB/c mice, with injection volume of 100 μl each mouse, 5 mice each group. In the HBsAg+Al(OH)$_3$ group, each mice was injected with 1 μg of HBsAg adsorbed with Al(OH)$_3$. In the HBsAg+HBcAg+CpG-ODN group, each mouse was injected with 1 μg HBsAg, 1 μg HBcAg and 2 μg CpG-ODN. Mice were immunized once every three weeks, and ten days after second immunization, the spleen was fetched. The splenic lymphocytes were prepared according to a conventional method, procedures as follows: aseptic spleen: cut the spleen using sterile forceps and scissors, put it in a 70 m nylon mesh sieve (purchased from BD Biosciences), and place it in 5 ml petri dish containing 2% pre-cooled FBS (purchased from GIBCO)-PBS. Grind the spleen using a grinding rod, and sieve the spleen cells into the dish, to get cell suspension. Pipette the suspension in a 50 ml sterile centrifuge tube filtered through 40 m nylon mesh sieve (purchased from BD Biosciences) by using a Pasteur pipette; 300×g, centrifuge 10 min at; discard the supernatant, add 5 ml 1× red-breaking agent (purchased from BD Biosciences) to re-suspend cells at room temperature for 5 minutes, to break the red blood cells. Add 5 ml 2% FBS-PBS to terminate the red breaking reaction; 300×g, centrifuge 5 min at 4. Remove the supernatant, add 2 ml of 2% FBS-PBS to re-suspend cells for standby. Detect the secretion of antigen-specific IFN-γ and IL-4 using Mouse IFN-γ/IL-4 ELISPOT Kits (BD Biosciences), with the stimulant of HBsAg peptide database. When the test was completed, read the number of spots from ImmunoSPOT Series 3 automatic plate reader.

HBsAg peptide library consists of 54 polypeptide fragments with 15 amino acids, covering the entire HBsAg full-length sequence, each pair of adjacent peptides have overlapping of 11 amino acids, representing all possible HBsAg CTL epitopes. The peptide fragment design of HBsAg peptide library was shown in SEQ ID NO:7~SEQ ID NO:60. The synthesis of all peptide fragments was carried out in Chinese Peptide Company, and then purified, subpackaged and lyophilized.

The procedure for detection on specific antigen specific IFN-γ and IL-4 secretion was as follows: Mouse IFN-γ/IL-4 was diluted with PBS (1:200 dilution, BD Biosciences), 100 μl/well, added to ELISPOT plates, coating overnight at 4.

Figure 7:
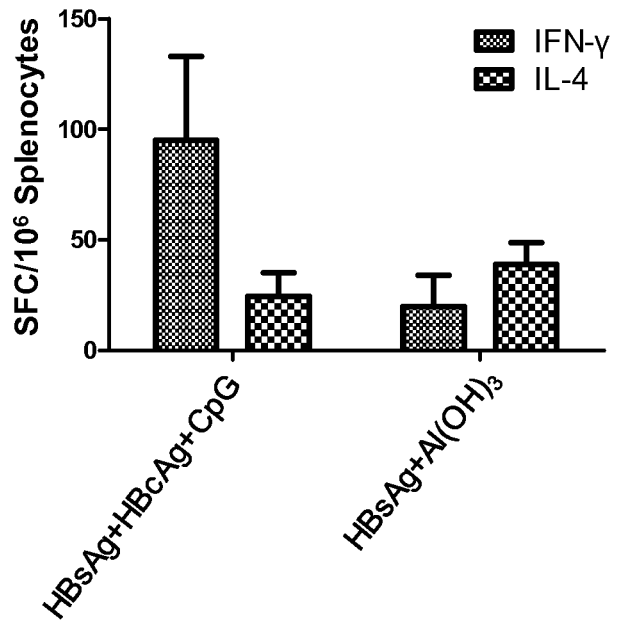
FIG. 7 shows that the composition of the present invention promotes HBsAg CTL epitope-specific Th1 cell differentiation and inhibits Th2 cell proliferation in the aspect of cell immunization when compared with the conventional vaccine components.

Discard the coated antibody, wash the well once using blocking solution (containing 10% FBS RPMI-1640 culture solution), add the blocking solution, 200 μl/well, and incubate 2 h at room temperature. Dilute the peptide library using 10% FBS-1640 culture medium to 10 μg/ml. Dilute ConA to 20 μg/ml using 10% FBS-1640 culture medium, used as the positive control. Discard the blocking solution, add 1×10$^7$ cells/ml of splenic lymphocyte suspension and the prepared peptide library o ConA control to the 96-well plate respectively, 100 μl/well, with repeat in two wells. Incubate them for 24 h in 5% $CO_2$ incubator at 37, discard the cell suspension, wash the plates twice using deionized water, 3~5 m/time, and wash 3 times using PBST, 200 μl/well, and then add Mouse IFN-γ/IL-4 ELISPOT detection Antibody diluted by 10% FBS PBS (1:250 dilution, BD Biosciences), 100 μl/well, and incubate 2 h at room temperature. Discard the detection antibody, wash the plates 4 times using PBST, 200 μl/well. Add Streptavidian-HRP (1:100 dilution, BD Biosciences) diluted by 10% FBS PBS, 100 μl/well, and incubate 1 h at room temperature. Discard the enzyme conjugate, wash 4 times using PBST, and then wash 3 times using PBS, add AEC substrate for coloration, 100 μl/well, observe the formation of spots visually, and add deionized water to terminate the reaction. Read the number of spots from ImmunoSPOT Series 3 automatic plate reader. The results were shown in FIG. 7.

The main antigens of Th1 cells specifically secrete IL-2, IL-12, IFN-γ and TNF-β, etc., to mediate the immune responses associated with cytotoxicity and local inflammation, involve in the cell-mediated immunity and the formation of delayed-type hypersensitivity inflammation. The main antigens of Th2 cells specifically secrete IL-4, IL-5, IL-6 and IL-10, whose main function is to stimulate the proliferation of B cells and produce antibody, associated with humoral immunity. IFN-γ can induce Th1 cell differentiation, but suppress the proliferation of Th2 cells; IL-4 can induce differentiation of Th2 cells. In this example, the antigen-specific IFN-γ and IL-4 secretion levels of spleen cells in immunized mice were detected by ELISPOT. Results showed that, Al(OH)$_3$, as the HBsAg adjuvant, could secrete HBsAg-specific IL-4 higher than IFN-γ, suggesting that Al(OH)$_3$ adjuvant mainly stimulated B cell proliferation to produce antibody. In the present invention, HBsAg+HBcAg+CpG-ODN composition could secrete HBsAg-specific IFN-γ much higher than IL-4, suggesting that the composition in the invention was mainly involved in HBsAg-specific cellular immunity, to promote the differentiation of Th1 cells and achieve the balance of Th1/Th2 cell proliferation. Therefore, it has the potential functions of killing HBV-infected liver cells and eliminating the free HBV viruses.

Example 8

The synergistic effect of combined HBsAg, HBcAg and CpG-ODN on producing antigen-specific IgG antibody In order to investigate whether the combined HBsAg, HBcAg and CpG-ODN has synergistic effect, the inventor mixed HBsAg, HBcAg and CpG-ODN to immunize the mice, determined the total HBsAg specific IgG and conducted statistical analysis, to evaluate whether antigen-specific IgG antibody producing from the combined HBsAg, HBcAg and CpG-ODN has the synergistic effect.

In the example, BALB/c mice were used, female, 6-8 weeks, purchased from Shanghai SLAC. The HBcAg, CpG-ODN and Al(OH)$_3$ adjuvant used in this example were as described in Example 1.

HBsAg and HBcAg were diluted with PBS to 10 μg/ml; CpG-ODN was diluted to 20 μg/ml with PBS. The left hind limb gastrocnemius was immunized for BALB/c mice, with injection volume of 100 μl each mouse, 10 mice each group.

In the HBsAg+CpG-ODN group, each mouse was injected with 1 μg HBsAg, and 2 μg CpG-ODN. In the HBsAg+HBcAg+CpG-ODN group, each mouse was injected with 1 μg HBsAg, 1 μg HBcAg and 2 μg CpG-ODN. Mice were immunized once every three weeks, and ten days after second immunization, blood was drawn to separate serum. The serum was diluted with 2% skim milk beginning from 1:30 dilution ratio according to conventional methods, then serially diluted 3-fold for detecting total antigen-specific IgG antibody.

The titers of HBsAg specific antibodies producing in HBsAg+HBcAg+CpG-ODN group and HBsAg+CpG-ODN group were determined using the method described in the Example 1. Results were shown in FIG. 8.

Figure 8:
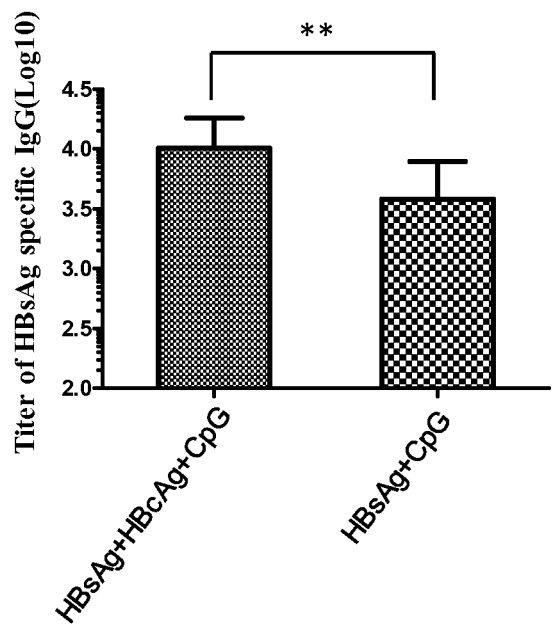
FIG. 8 shows that the combination of HBcAg and HBsAg+CpG in the composition of the present invention has synergistic effects at the level of producing antigen-specific IgG antibody.

As shown from FIG. 8, the titer of HBsAg specific antibody in the combined HBcAg, HBsAg and CpG-ODN group was higher than that in the HBsAg+CpG-ODN group, which could be as high as 4.0 log value, showing significant difference ($P<0.01$) and the titer of specific antibody could increase by about 3-fold. The results showed that, after adding HBcAg, the HBsAg+HBcAg+CpG-ODN composition could produce significantly high HBsAg specific IgG antibody than HBsAg+CpG-ODN, demonstrating that HBcAg, HBsAg and CpG-ODN have synergistic effect.

Example 9

The combined HBcAg, HBsAg and CpG-ODN could promote HBsAg-specific Th1 cell differentiation in terms of cell-mediated immunity compared with HBsAg+CpG-ODN.

In the example 8, the synergistic effect of HBcAg, HBsAg and CpG-ODN was investigated in terms of humoral immunity. The inventor analyzed whether the combined HBcAg, HBsAg and CpG-ODN could promote the Th1 cell differentiation of HBsAg in terms of cell-mediated immunity, to further verify the synergistic effect of HBcAg, HBsAg and CpG-ODN.

The HBsAg, HBcAg and CpG-ODN, HBsAg and CpG-ODN adjuvant were mixed respectively, to immunize the mice. Through detection on the IFN-γ and IL-4 secretion level by the ELISPOT experiment, the promotion on Th1 cell differentiation by HBsAg of combined HBsAg HBcAg, with CpG-ODN could be evaluated compared with the combined HBsAg+CpG-ODN.

In the example, BALB/c mice were used, female, 6-8 weeks, purchased from Shanghai SLAC. The HBsAg, HBcAg, CpG-ODN used in this example were as described in example 1.

HBsAg and HBcAg were diluted with PBS to 10 μg/ml; CpG-ODN was diluted to 20 μg/ml with PBS. The left hind limb gastrocnemius was immunized for BALB/c mice, with injection volume of 100 μl each mouse, 10 mice each group.

In the HBsAg+CpG-ODN group, each mouse was injected with 1 μg HBsAg, and 2 μg CpG-ODN. In the HBsAg+HBcAg+CpG-ODN group, each mouse was injected with 1 μg HBsAg, 1 μg HBcAg and 2 μg CpG-ODN. Mice were immunized once every three weeks, and ten days after second immunization, the spleen was fetched. The splenic lymphocytes were prepared according to a conventional method. IFN-γ and IL-4 were detected by Moμse IFN-γ/IL-4 ELISPOT Kits (BD Biosciences). The stimulant was HBsAg peptide library (specific sequence was as described in Example 7). When the experiment was completed, the number of spots was read from Immuno-SPOT Series 3 automatic plate reader.

The secretion level of HBsAg epitope-specific IFN-γ and IL-4 of spleen cells in the HBsAg+HBcAg+CpG-ODN composition the present invention and HBsAg+CpG-ODN group. Results were shown in FIG. 9.

Figure 9:
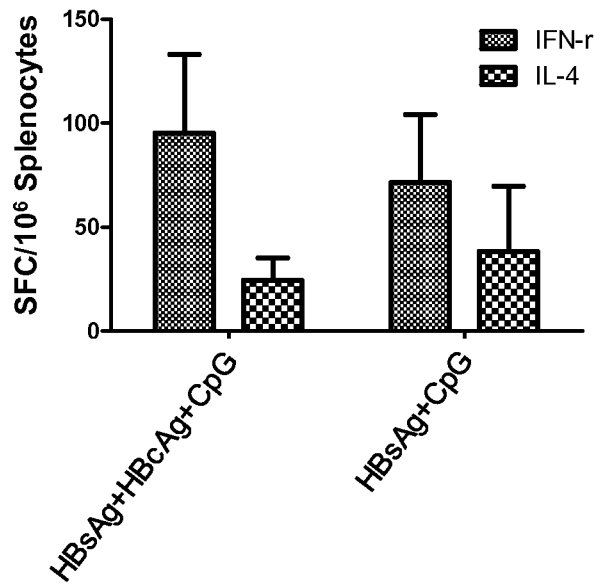
FIG. 9 shows that the combination of HBcAg and HBsAg+CpG in the composition of the present invention has the ability of promoting HBsAg-specific Th1 cell differentiation at the level of cellular immunity when compared with HBsAg+CpG.

As shown from FIG. 9, the combined HBcAg and HBsAg+CpG-ODN had a higher secretion of HBsAg-specific IFN-γ than that in the HBsAg+CpG-ODN group, but the HBsAg-specific IL-4 was lower, suggesting that the HBsAg+HBcAg+CpG-ODN composition could promote the differentiation of HBsAg-specific Th1 cells in terms of cell-mediated immunity compared with combined HBsAg+CpG-ODN, indicating that HBcAg, HBsAg and CpG-ODN had a synergistic effect.

Example 10

HBsAg+HBcAg+CpG-ODN composition broke through immune tolerance of HBV transgenic mice (adr serotype) and mice with immune tolerance (B10.M).

In order to verify whether the combined HBsAg+HBcAg+CpG-ODN could break through immune tolerance in HBV transgenic mice and mice with immune tolerance, the inventor mixed the HBsAg, HBcAg and CpG-ODN, HBsAg and Al(OH)$_3$ adjuvant to immunize mice, and determine the total HBsAg-specific IgG and protective antibody IU level in serum, and conduct statistical processing, to evaluate the influence of combined HBsAg+HBcAg+CpG-ODN on breakthrough of immune tolerance compared with combined HBsAg and Al(OH)$_3$.

In this example, two kinds of mice of immune tolerance were used. The first kind was HBV transgenic mice, serotype adr, male, 10-12 weeks, purchased from Shanghai Southern Model Animal Center; and the second kind was B10.M mice, mice with histocompatibility, with immune tolerance, male, 6-8 weeks, purchased from The Jackson Laboratory; the HBsAg, HBcAg and, CpG-ODN and Al(OH)$_3$ adjuvant were as described in Example 1.

HBsAg and HBcAg were diluted with PBS to 10 μg/ml; CpG-ODN was diluted to 20 μg/ml with PBS. The left hind limb gastrocnemius was immunized for mice, with injection volume of 100 μl each mouse, 4 mice each group.

In the HBsAg+Al(OH)$_3$ group, each mice was injected with 1 μg of HBsAg adsorbed with Al(OH)$_3$. In the HBsAg+HBcAg+CpG-ODN group, each mouse was injected with 1 μg HBsAg, 1 μg HBcAg and 10 μg CpG-ODN. Mice were immunized once every three weeks, and two weeks after each immunization, blood was drawn, a total of 6 times of immunization. The total antigen-specific IgG antibody was detected according to the method in the Example 2. Results were shown in FIG. 10. The HBsAg antibody produced according to above method in the Example 2 was detected, and results were shown in FIG. 11.

Figure 10:
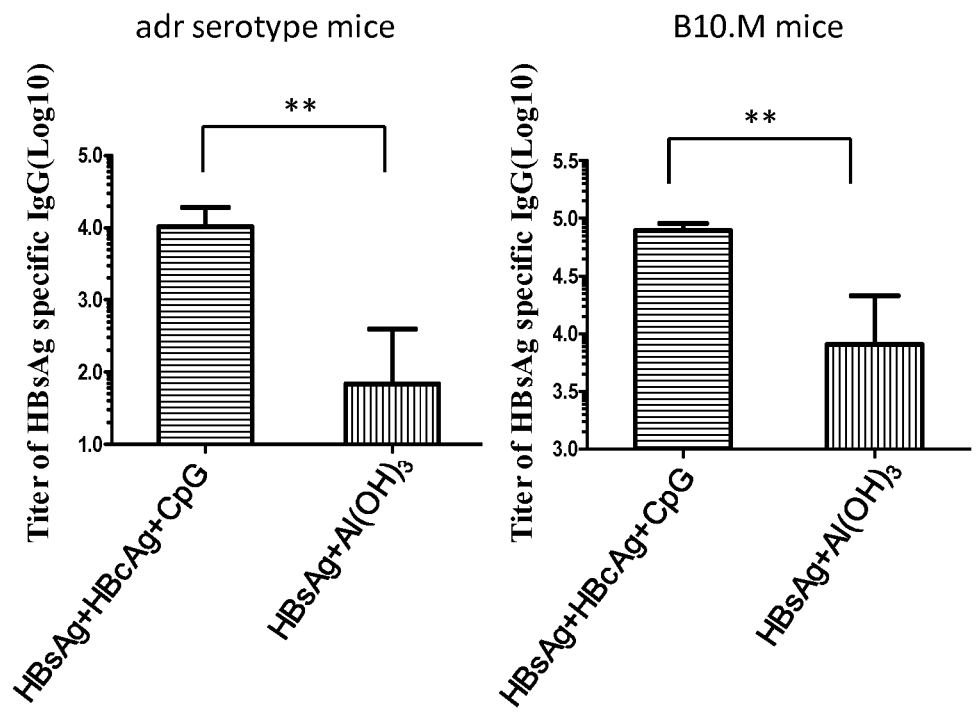
FIG. 10 shows that the composition of the present invention breaks through immune tolerance of HBV transgenic mice and immune tolerance mice in producing antigen-specific IgG immune response.
Figure 11:
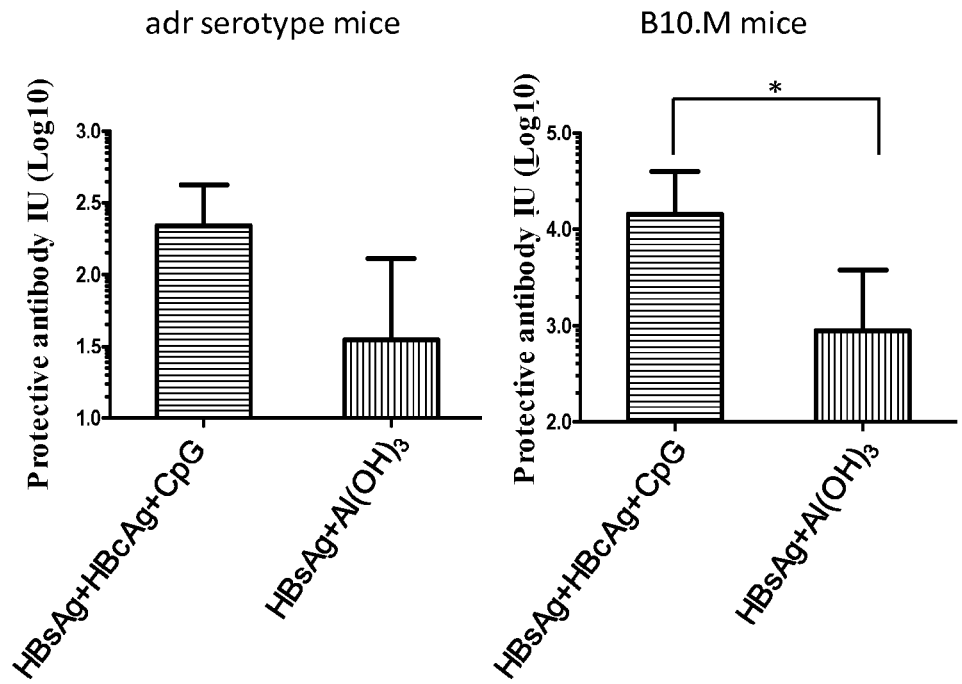
FIG. 11 shows that the composition of the present invention breaks through immune tolerance of HBV transgenic mice and immune tolerance mice in producing neutralizing antibody immune response.

As shown from FIG. 10, HBsAg+HBcAg+CpG-ODN composition could break through the immune tolerance of two kinds of model mice. The titer of HBsAg-specific IgG antibody could be higher than 4.0 log value, showing significant difference compared with HBsAg+Al(OH)$_3$ group (P<0.05). The titer of HBsAg-specific IgG antibody could be increased by 10-200 times. As seen from FIG. 11, the protective antibody level could be up to 2.5 log value, compared with HBsAg+Al(OH)$_3$ group, the produced protective antibody level was increased by 5-20 times. The above results showed that, the HBsAg+HBcAg+CpG-ODN vaccine could significantly enhance the immune response of total HBsAg-specific IgG and protective antibodies in mice with immune tolerance compared with Al(OH)$_3$ adjuvant hepatitis B vaccine, and break through the immune tolerance more effectively.

Example 11

HBsAg+HBcAg+CpG-ODN composition produced high titer of anti-HBcAg-specific IgG antibodies in HBV transgenic mice (adr serotype) and mice with immune tolerance (B10.M)

In order to verify whether the combined HBsAg+HBcAg+CpG-ODN produced anti-HBcAg-specific IgG antibodies in HBV transgenic mice and mice with immune tolerance, the inventor mixed HBsAg, HBcAg and CpG-ODN to immunize the mice, and determine total HBcAg-specific IgG level in the serum.

Two kinds of mice with immune tolerance were used, as described in Example 10. The HBsAg, HBcAg and CpG-ODN used were as described in Example 1.

HBsAg and HBcAg were diluted with PBS to 10 μg/ml; CpG-ODN was diluted to 20 μg/ml with PBS. The mice were injected with 1 μg HBsAg, 1 μg HBcAg and 10 μg CpG-ODN via left hind limb gastrocnemius, with injection volume of 100 μl each mouse, 4 mice each group. Mice were immunized once every three weeks, and two weeks after each immunization, blood was drawn, a total of 6 times of immunization. The total HBcAg-specific IgG antibody was detected according to the method in the Example 1, the difference was that the coated antigen was 1 μg HBcAg antigen, results were shown in FIG. 12.

Figure 12:
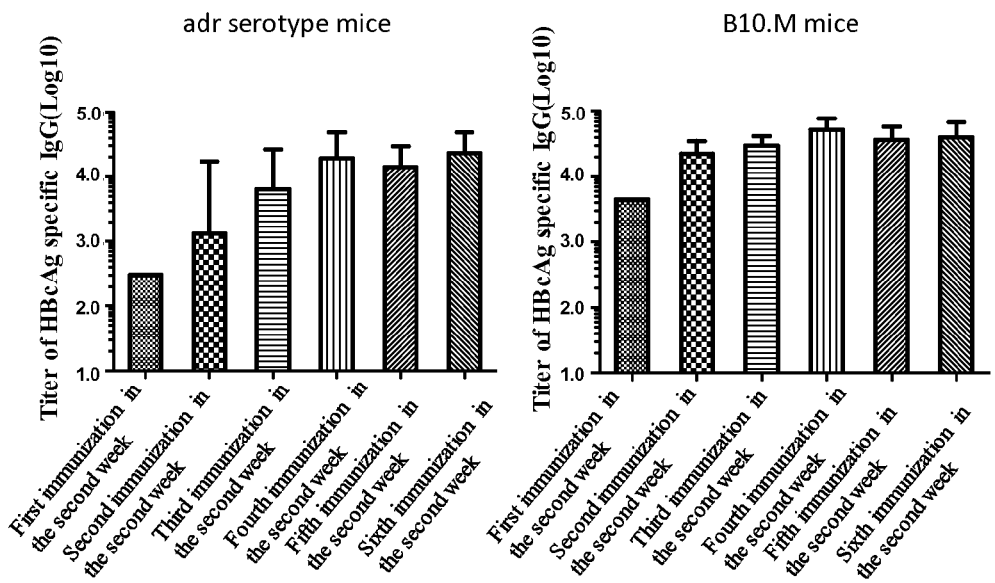
FIG. 12 shows that the composition of the present invention produces anti-HBcAg specific IgG antibody with high-titer in breaking through immune tolerance of HBV transgenic mice and immune tolerance mice.

As shown from FIG. 12, the HBsAg+HBcAg+CpG-ODN composition can be used in two kinds of model mice, to produce two kinds of high-titer of anti-HBcAg-specific IgG antibody. Two weeks after the primary immunization, the titer of antibody could reach over 2.5 log value, thereafter the titer of antibody could reach over 4.0 log value. These results showed that, the HBsAg+HBcAg+CpG-ODN composition in the present invention could produce high-titer anti-HBcAg specific IgG antibody.

Example 12

HBsAg+HBcAg+CpG-ODN composition produced anti-HBcAg antibody subtypes (IgG2a>IgG1) in HBV transgenic mice (adr serotype) and mice with immune tolerance (B10.M).

In order to verify that the HBsAg+HBcAg+CpG-ODN composition produced anti-HBcAg antibody subtypes (IgG2a>IgG1) in HBV transgenic mice (adr serotype) and mice with immune tolerance (B10.M), the inventor mixed HBsAg, HBcAg and CpG-ODN to immunize the mice and determine the titers of anti-HBcAg antibody subtype IgG2a and IgG1 in serum.

Two kinds of mice with immune tolerance were used in this Example, as described in Example 10. The HBsAg, HBcAg and CpG-ODN used were as described in Example 1.

HBsAg and HBcAg were diluted with PBS to 10 μg/ml; CpG-ODN was diluted to 20 μg/ml with PBS. The mice were injected with 1 μg HBsAg, 1 μg HBcAg and 10 μg CpG-ODN via left hind limb gastrocnemius, with injection volume of 100 μl each mouse, 4 mice each group. Mice were immunized once every three weeks, and two weeks after each immunization, blood was drawn, a total of 6 times of immunization. The titers of anti-HBcAg antibody subtype IgG2a and IgG1 in serum were determined using the methods as described in Example 6. Results were shown in FIG. 13.

Figure 13:
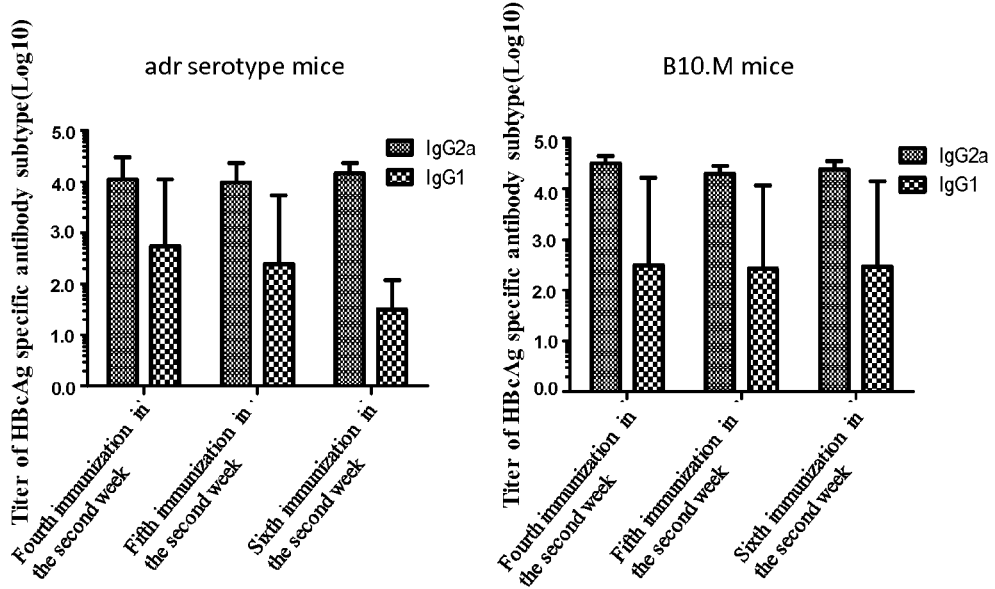
FIG. 13 shows that the anti-HBcAg antibody subtype generated by the composition of the present invention in the HBV transgenic mice and immune tolerance mice is IgG2a>IgG1.

Results in FIG. 13 showed that, HBsAg+HBcAg+CpG-ODN composition in the present invention produced anti-HBcAg antibody subtypes (IgG2a>IgG1) in HBV transgenic mice (adr serotype) and mice with immune tolerance (B10.M), showing significant difference (P<0.01).

Example 13

HBsAg+HBcAg+CpG-ODN composition had the tendency of clearing away HBsAg antigen in HBV transgenic mice.

The HBsAg+HBcAg+CpG-ODN composition broke through immune tolerance of HBV transgenic mice and produced antigen-specific antibodies. We performed analysis on them and investigated whether the in vivo HBsAg expression showed a downward trend, and validated the elimination of HBsAg antigens by antibody in the serum.

In the example, HBV transgenic mice were used, serotype adr (transformed from C57 mice), male, 10-12 weeks, purchased from Shanghai Southern Model Animal Center. The HBsAg, HBcAg, CpG-ODN and Al(OH)$_3$ adjuvant used were as described in Example 1.

HBsAg and HBcAg were diluted with PBS (Invitrogen Corporation) to 10 µg/ml and 100 µg/ml respectively; CpG-ODN was diluted to 20 µg/ml and 200 µg/ml with PBS, respectively. The left hind limb gastrocnemius was immunized for the mice, with injection volume of 100 µl each mouse, 8 mice each group. In the HBsAg+Al(OH)$_3$ group, each mice was injected with 1 µg of HBsAg adsorbed with Al(OH)$_3$. The HBsAg+HBcAg+CpG-ODN group was divided into two subgroups, each mouse in the one subgroup was injected with 1 µg HBsAg, 1 µg HBcAg and 10 µg CpG-ODN. And in the other subgroup, each mouse was injected with 10 µg HBsAg, 10 µg HBcAg and 20 µg CpG-ODN. Mice were immunized once every three weeks, and two weeks after each immunization, blood was drawn, a total of 6 times of immunization. The serum before immunization and two weeks after the sixth immunization was diluted with 2% skim milk at 1:200 dilution ratio according to conventional methods. The HBsAg antigen as described in Emgobimetn 1 was used as the standard substance. The serum of C57 mice (purchased from Shanghai SLAC) was diluted according to the starting concentrations of 1000 ng/ml, 500 ng/ml, 250 ng/ml, 125 ng/ml, 62.5 ng/ml, 31.25 ng/ml, 15.625 ng/ml and 7.8 ng/ml, and then diluted at 1:200 using 2% skimmed milk. The HBsAg antigen concentrations of the diluted sample and standard substance were detected using HBsAg antigen detection kits (Shanghai Kehua). The HBsAg antigen concentration in the serum of mice before immunization and two weeks after the sixth immunization was calculated using the measured standard curve, and the antigen HBsAg decline % two weeks after the sixth immunization was calculated. Results were shown in FIG. 14.

Specific procedures for the detection of HBsAg antigen concentration were as follows: take out the pre-coated anti-HBsAg reaction plate, add 75 µl of diluted serum, negative and positive controls in the reaction holes; after covering the reaction plate with a sticking paper, the reaction plate was placed at 37° C. for incubation 1 h. Take out the reaction plate and remove the sticking paper, and add 50 µl enzyme conjugate in the samples to be tested and the positive and negative control holes; shake them on a microporous oscillator for 10 s. After covering the reaction plate with a sticking paper, the reaction plate was placed at 37° C. for incubation 30 min. Take out the reaction plate and remove the sticking paper, wash the reaction plate 5 times. At the end of washing, immediately add color developing agent A and color developing agent B to all holes, 50 µl each, and mix them evenly; then shake them on a microporous oscillator for 10 s. After covering the reaction plate with a sticking paper, the reaction plate was placed at 37'C for incubation 30 min. Add 50 µl stop solution to all holes, shake to react 5 s and mix well. Determine the OD$_{450nm}$ value with a enzyme-link meter (corrected at OD$_{630nm}$).

Figure 14:
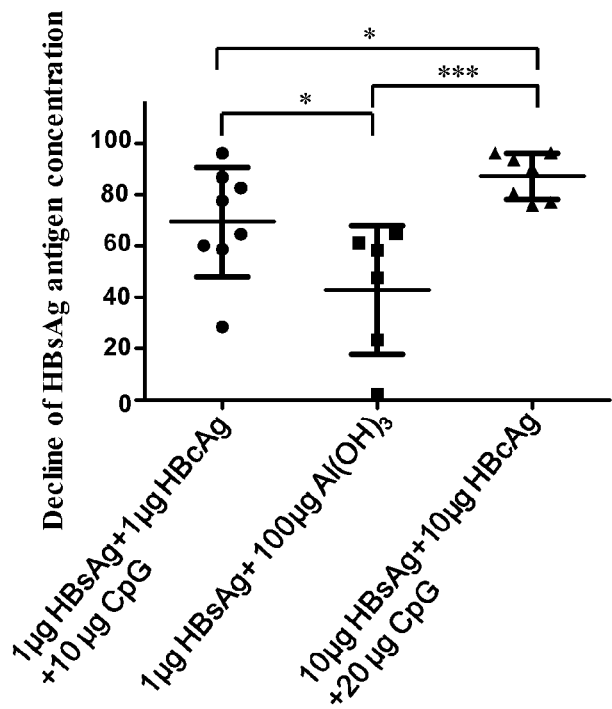
FIG. 14 shows the stronger ability of the composition of the present invention in eliminating HBsAg antigen in HBV transgenic mice compared with conventional vaccine compositions.

Referring to FIG. 14, the HBsAg antigen concentration decline percent in HBV transgenic mice in the HBsAg+HBcAg+CpG-ODN composition group was higher than that of HBsAg+Al(OH)$_3$ group, with significant differences (P<0.05); after enhancing the doses of HBsAg, HBcAg and CpG-ODN adjuvant, the HBsAg antigen concentration decline percent was more apparent, as high as over 90% on average, suggesting that, the composition could eliminate the HBsAg antigen to convert HBsAg antigen to negative, laying a solid foundation for the therapeutic vaccines of chronic hepatitis B.

Example 14

HBsAg+HBcAg+CpG-ODN composition has an in vivo killing activity of HBsAg and HBcAg antigen-specific CTL.

The in vivo killing of antigen-specific CTL is the most direct evidence of effect of therapeutic vaccines. By detecting the in vivo killing activity of HBsAg and HBcAg antigen-specific CTL in mice immunized with HBsAg+HBcAg+CpG-ODN composition, the in vivo killing activity of CTL was validated and the CTL killing rate was calculated.

In the example, C57BL/6J mice were used, female, 6-8 weeks, purchased from Shanghai SLAC. The HBsAg antigen, HBcAg and CpG-ODN adjuvant used in this example were as described in Example 1.

HBsAg and HBcAg were diluted with PBS to 100 µg/ml; CpG-ODN was diluted to 200 µg/ml with PBS. The left hind limb gastrocnemius was immunized for the mice, with injection volume of 100 µl each mouse, 8 mice each group. In the HBsAg+HBcAg+CpG-ODN group, each mouse was injected with 10 µg HBsAg, 10 µg HBcAg and 20 µg CpG-ODN. Mice were immunized once every two weeks, a total of three times of immunization. Ten days after third immunization, the in vivo killing activity of HBsAg and HBcAg antigen-specific CTL was detected, and results were shown in FIG. 15.

Specific detection steps of in vivo killing activity of HBsAg and HBcAg antigen-specific CTL were as follows: Fetch the spleen of non-immunized mouse under a sterile state, grind it in a glass slide, 300×g, centrifuge at 4° C. for 5 min, and remove the supernatant. Add 5 ml erythrocyte lysis buffer (purchased from BD Biosciences) and re-suspend the cells, place 5 min at room temperature to lyse the red blood cells, wash them twice using 10 ml PBS (purchased from GIBCO company). Dilute CFSE (purchased from Molecular Probes Inc.) using PBS to 4 M and 0.4 µM, and mix with equal volume of cell suspension evenly, place still at room temperature for 7 min, 300×g, centrifuge at 4° C. for 5 min, and remove the supernatant. Wash it twice with PBS. Re-suspend the cells using RPMI-1640 (purchased from GIBCO Company) complete medium, to reach the cell concentration at 2×10$^7$ cells/ml. Add equal volume of HBsAg peptide library (see Example 7) and HBcAg peptide library to CFSE$^{high}$ respectively. Add equal volume of RPMI-1640 complete medium to the CFSE$^{low}$ cells, transfer them to the cell culture flasks, place still 4 h at 37, 5% CO$_2$ incubator; wash it twice using PBS, and resuspend the cells with PBS and count them. Adjust the cells to 2×10$^7$ cells/ml using PBS according to the counting results, then mix the two groups of cells in equal volume. Inject the prepared mixture of labeled cells to the mice immunized with HBsAg+HBcAg+CpG-ODN via orbits, 100 μl each mouse. 15~17 h later, prepare the spleen cell suspension, and re-suspend cells using 2% FBS-PBS, detect it by flow cytometry; and calculate the killing percent of antigen-specific CTL.

The above HBcAg peptide library was composed of 43 polypeptide fragments with 15 amino acids covering the entire HBcAg full-length sequence; each pair of adjacent peptides have 11 overlapping amino acids, representing all possible HBcAg CTL epitopes, such as the amino acid fragment at the 1-15 positions, 5-19 positions, 9-23 positions . . . 169-183 positions in SEQ ID NO:2. The peptide segments of the above HBcAg peptide library were as shown in SEQ ID NO: 61~SEQ ID NO: 103. All peptide segments were synthesized, purified, sub-packaged and lyophilized by Chinese Peptide Company.

Figure 15:
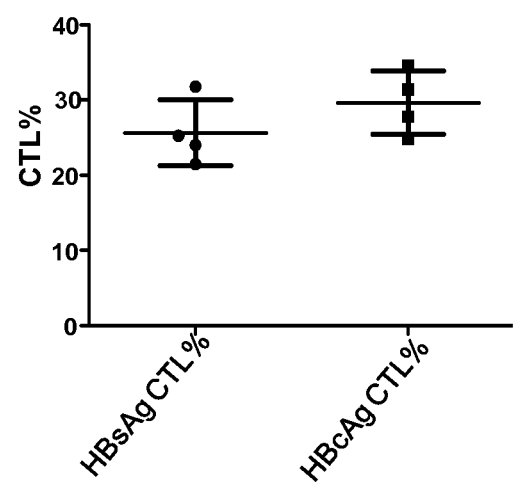
FIG. 15 shows that the composition of the present invention has the in vivo killing activity of HBsAg and HBcAg antigen-specific CTL, proving that the composition of the present invention can be used as a therapeutic vaccine of chronic hepatitis B.

By referring to FIG. 15, HBsAg+HBcAg+CpG-ODN composition has an in vivo killing activity of HBsAg and HBcAg antigen-specific CTL in C57BL/6J mice, and its CTL killing rate was about 30%, suggesting that this composition has in vivo killing activity of HBsAg and HBcAg antigen-specific CTL, providing the most direct evidence for the therapeutic vaccines of chronic hepatitis B.

In the present application, multiple publications are referenced in the parentheses. Accordingly, the disclosures of these publications are incorporated herein by reference in entirety, to state the state of the arts related to this invention in a more complete way.

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications and alterations may be applied to the compositions and/or methods described herein without departing from the true spirit, concept and scope of the invention.

The invention claimed is:

1. A pharmaceutical composition consisting of:
   i) hepatitis B surface antigen (HBsAg),
   ii) hepatitis B core antigen (HBcAg),
   iii) CpGoligodeoxynucleotide (CpG-ODN), and
   iv) optionally a pharmaceutically acceptable carrier,
wherein the CpG-ODN sequence is selected from the following: 5'-TCG TTC GTT CGT TCG TTC GTT-3' (SEQ ID NO: 3), 5'-TCG TTC GTT CGT TCG TTC GTT CGT T-3' (SEQ ID NO: 4), 5'-TCG TCG TCGTCGTCGTCG TCG-3' (SEQ ID NO: 5) and 5'-TCC ATG ACG TTC CTG ACG TT-3' (SEQ ID NO: 6).

2. The pharmaceutical composition according to claim 1, wherein the pharmaceutical composition is administered prophylactically or therapeutically.

3. The pharmaceutical composition according to claim 1, wherein the HBsAg has the sequence as shown in SEQ ID NO:1.

4. The pharmaceutical composition according to claim 1, wherein the HBcAg has the sequence as shown in SEQ ID NO:2.

5. The pharmaceutical composition according to claim 1, wherein the CpG-ODN sequence has the sequence: 5'-TCG TTC GTT CGT TCG TTC GTT-3' (SEQ ID NO:3).

6. The pharmaceutical composition according to claim 1, wherein the range of the relative weight ratio of the components i), ii) and iii) in the said pharmaceutical composition is 1:0.2~5: 1~50.

7. A kit, comprising a pharmaceutical composition according to claim 1 and instructions for use thereof.

8. A method for generating immune response against HBV by administering to a subject a pharmaceutical composition according to claim 1.

9. The pharmaceutical composition according to claim 6, wherein the range of the relative weight ratio of the components i), ii) and iii) in the said pharmaceutical composition is 1:1-5:2-15.

* * * * *